United States Patent
White

(10) Patent No.: US 12,079,423 B2
(45) Date of Patent: Sep. 3, 2024

(54) RAPIDLY CAPTURING USER INPUT

(71) Applicant: TREES TECHNOLOGY COMPANY, San Luis Obispo, CA (US)

(72) Inventor: Jonathan White, San Luis Obispo, CA (US)

(73) Assignee: Jonathan White, San Luis Obispo, CA (US)

(*) Notice: Subject to any disclaimer, the term of this patent is extended or adjusted under 35 U.S.C. 154(b) by 0 days.

(21) Appl. No.: 17/751,390

(22) Filed: May 23, 2022

(65) Prior Publication Data

US 2022/0382450 A1    Dec. 1, 2022

Related U.S. Application Data

(60) Provisional application No. 63/194,172, filed on May 27, 2021.

(51) Int. Cl.
  *G06F 3/041*    (2006.01)
  *G06F 3/0482*   (2013.01)
  *G06F 3/0488*   (2022.01)

(52) U.S. Cl.
  CPC ...... *G06F 3/041661* (2019.05); *G06F 3/0482* (2013.01); *G06F 3/0488* (2013.01)

(58) Field of Classification Search
  CPC ........ G16H 40/63; G16H 50/30; G16H 50/50; G16H 10/20; G06F 3/041661;
  (Continued)

(56) References Cited

U.S. PATENT DOCUMENTS 5,810,605 A   9/1998  Siefert
7,311,666 B2  12/2007 Stupp
(Continued)

FOREIGN PATENT DOCUMENTS

CN   102122294   7/2011
CN   106485562   3/2017
(Continued)

OTHER PUBLICATIONS

Instagram Blog Post; "Introducing the Emoji Slider Sticker for Instagram Stories"; https://about.instagram.com/blog/announcements/introducing-the-emoji-slider-sticker#:~:text=Today%2C%20we're%20introducing%20the,%F0%9F%8C%B6%20they%20like%20their%20food.; May 10, 2018; 6 pages.

(Continued)

*Primary Examiner* — Olga V Merkoulova

(74) *Attorney, Agent, or Firm* — Fitch, Even, Tabin & Flannery LLP

(57) ABSTRACT

The present disclosure describes systems and methods for rapidly capturing user input. Some embodiments of the present disclosure may rapidly capture user input for psychometric analysis applications. For example, a Likert scale may be used to capture the intensity of feelings of a respondent for a given item or question, and therefore can be applied to multiple domains including psychology and social sciences, business and marketing, etc. According to techniques described herein, a visual display screen may prompt respondent input (e.g., via an input prompt, question, statement, etc.). A touch-sensitive input area of the visual display screen may capture respondent input. The touch-sensitive input area may include an input bar and an input position (e.g., a slider). A respondent may control the input position along the input bar (e.g., using a finger), such that the input capture system may efficiently capture, determine, and record the input.

21 Claims, 17 Drawing Sheets

(58) Field of Classification Search
CPC ............ G06F 3/04847; G06F 3/04883; G06F 3/0488; G06F 3/04886; G06F 3/041; G06F 3/0482
See application file for complete search history.

(56) References Cited

U.S. PATENT DOCUMENTS

| | | | |
|---|---|---|---|
| 7,330,823 | B1 | 2/2008 | Derosier |
| 7,899,700 | B2 | 3/2011 | Floyd |
| 8,032,398 | B1 | 10/2011 | Kelly |
| 8,208,399 | B2* | 6/2012 | Yariv ............... G06F 3/04847 370/252 |
| 8,210,431 | B2 | 7/2012 | Earl |
| 8,515,780 | B2 | 8/2013 | Soto |
| 8,769,080 | B2 | 7/2014 | Cancel |
| 8,805,759 | B1 | 8/2014 | Cha |
| 8,806,385 | B1* | 8/2014 | Rinckes ............ G06F 3/04847 345/173 |
| 8,825,580 | B2 | 9/2014 | Brillhart |
| 8,909,587 | B2 | 12/2014 | Alush |
| 8,965,780 | B2 | 2/2015 | Carsanaro |
| 8,977,678 | B2 | 3/2015 | Jarville |
| 8,979,646 | B2 | 3/2015 | Moser |
| 9,020,845 | B2* | 4/2015 | Marlowe ............ G06Q 30/0643 705/27.2 |
| 9,092,799 | B2 | 7/2015 | Simpson |
| 9,262,768 | B2 | 2/2016 | Carsanaro |
| 9,264,776 | B2* | 2/2016 | Jung ............... H04N 21/47217 |
| 9,398,450 | B2 | 7/2016 | Ludwig |
| 10,115,172 | B2 | 10/2018 | Goldberg |
| 10,140,883 | B2 | 11/2018 | Wong |
| 10,176,640 | B2 | 1/2019 | Tierney |
| 10,222,961 | B2 | 3/2019 | Rosenberg |
| 10,430,497 | B2 | 10/2019 | Williams |
| 10,460,617 | B2 | 10/2019 | Lin |
| 10,496,247 | B2 | 12/2019 | Badereddin |
| 10,521,503 | B2 | 12/2019 | Kopikare |
| 10,524,713 | B2 | 1/2020 | Valacich |
| 10,637,905 | B2* | 4/2020 | Wang ............... H04L 65/4015 |
| 10,877,632 | B2 | 12/2020 | Sarin |
| 10,891,635 | B2 | 1/2021 | Montoya |
| 10,949,754 | B2 | 3/2021 | Cohen-Zur |
| 11,275,446 | B2* | 3/2022 | Franklin ............ G06F 21/32 |
| 11,755,194 | B2* | 9/2023 | Chow ............... H04L 67/02 345/173 |
| 2006/0253800 | A1 | 11/2006 | Jones |
| 2007/0111189 | A1 | 5/2007 | Nelson |
| 2008/0301551 | A1 | 12/2008 | Gluck |
| 2009/0153288 | A1* | 6/2009 | Hope ............... H04N 21/42204 340/5.1 |
| 2011/0130170 | A1* | 6/2011 | Han ............... G06F 3/041 455/566 |
| 2011/0153383 | A1 | 6/2011 | Bhattacharjya |
| 2012/0016678 | A1 | 1/2012 | Gruber |
| 2012/0171648 | A1 | 7/2012 | Price |
| 2013/0005312 | A1 | 1/2013 | Roundtree |
| 2014/0074848 | A1 | 3/2014 | Kettunen |
| 2014/0108999 | A1* | 4/2014 | Chiu ............... G06F 3/04883 715/786 |
| 2014/0278786 | A1 | 9/2014 | Liu-Qiu-Yan |
| 2014/0358637 | A1 | 12/2014 | Kahneman |
| 2014/0372269 | A1 | 12/2014 | Ternan |
| 2015/0066602 | A1 | 3/2015 | Windsor |
| 2015/0326688 | A1* | 11/2015 | Aarnio ............. H04L 67/30 707/748 |
| 2016/0132604 | A1 | 5/2016 | Brust |
| 2016/0378316 | A1 | 12/2016 | Jakubiec |
| 2017/0102834 | A1 | 4/2017 | Moszczynski |
| 2017/0188976 | A1 | 7/2017 | Kalra |
| 2018/0115899 | A1 | 4/2018 | Kedem |
| 2018/0276355 | A1 | 9/2018 | Barday |
| 2018/0349583 | A1 | 12/2018 | Turgeman |
| 2018/0374560 | A1 | 12/2018 | Paty |
| 2019/0042081 | A1 | 2/2019 | Rosenberg |
| 2019/0146651 | A1* | 5/2019 | Williams ............ G06F 3/0482 715/720 |
| 2019/0149885 | A1* | 5/2019 | Madison ............ H04N 21/4312 715/838 |
| 2019/0179526 | A1* | 6/2019 | Yellen ............... G11B 27/00 |
| 2019/0333629 | A1 | 10/2019 | Torres |
| 2020/0150752 | A1 | 5/2020 | Kuntagod |
| 2020/0348836 | A1* | 11/2020 | Adem ............... G06F 3/017 |

FOREIGN PATENT DOCUMENTS

| | | |
|---|---|---|
| CN | 107071527 | 8/2017 |
| EP | 3054836 | 8/2016 |
| EP | 3058523 | 8/2016 |
| WO | 199022323 | 5/1999 |
| WO | 2015063542 | 5/2015 |

OTHER PUBLICATIONS

Isa; "New app a 'game changer' to guage realistic drinking habits"; Jul. 18, 2019; https://www.abc.net.au/news/2019-07-19/drinking-app-game-changer-for-indigenous-communities/11313562?nw=0.

ISurvey & droidSurvey App; Harvest Your Data; "What would it mean to your business if we could increase your repeat sales and keep your clients happy while providing you with time saving data collection tools that eliminate paper?"; https://www.harvestyourdata.com/features/.

Jacobs et al; "A survey tool for measuring evidence-based decision making capacity in public health agencies"; BMC Health Services Research 2012; https://www.biomedcentral.com/1472-6963/12/57; (Year: 2012); 9 pages.

Lee et al.; "Developing a tablet computer-based application ('App') to measure self-reported alcohol consumption in Indigenous Australians"; BMC Medical Informatics and Decision Making; (Year: 2018); 11 pages.

Whoop Strain; https://www.whoop.com/experience/strain/; Downloaded Jun. 3, 2022; 7 pages.

Whoop; Personalized Fitness and Activity Tracking; WayBack Machine; http://web.archive.org/web/20201021140452/https://www.whoop.com/experience/strain/; Oct. 21, 2020; 7 pages.

* cited by examiner

RAPIDLY CAPTURING USER INPUT

This application claims the benefit of U.S. Provisional Application No. 63/194,172, filed May 27, 2021, for RAPIDLY CAPTURING USER INPUT, which is incorporated in its entirety herein by reference.

BACKGROUND OF THE INVENTION

1. Field of the Invention

The present invention relates generally to prompting user input, and more specifically to rapidly capturing user input.

2. Discussion of the Related Art

Various systems and processes are known in the art for rapidly capturing user input.

Psychometric analysis refers to the techniques of psychological measurement which includes the conscious and unconscious phenomena of the mind and behavior. In some cases, psychometric analysis concerns with the measurement of skills and knowledge, attitudes, personality traits, etc., using assessment instruments, for example, questionnaires, personality tests, etc.

Psychometric analysis may include use of raw scores derived from assessments as measurements. In some examples, methods based on covariance matrices are used for measurement. Covariance matrices-based methods develop associations between raw scores. Other cases use measurement models which construct procedures or operations that meet certain criteria. Furthermore, tests are conducted to ascertain whether the relevant criteria have been met.

However, conventional methods for psychometric analysis may not provide a method to efficiently measure the intensity of feelings of a respondent for a given question set. Therefore, there is a need in the art for improved systems and methods to efficiently (e.g., and rapidly) capture user input (e.g., in response to psychometric analysis questionnaires).

SUMMARY

The present disclosure describes systems and methods for rapidly capturing user input. Some embodiments of the present disclosure may rapidly capture user input for psychometric analysis applications. For example, a Likert scale may be used to capture the intensity of feelings of a respondent for a given item or question, and therefore can be applied to multiple domains including psychology and social sciences, business and marketing, etc. According to techniques described herein, a visual display screen may prompt respondent input (e.g., via an input prompt, question, statement, etc.). A touch-sensitive input area of the visual display screen may capture respondent input. The touch-sensitive input area may include an input bar and an input position (e.g., a slider). A respondent may control the input position along the input bar (e.g., using a finger), such that the input capture system may efficiently capture, determine, and record the input.

An apparatus, system, and method for rapidly capturing user input are described. One or more embodiments of the apparatus, system, and method include a visual display screen having a surface area, a housing having an edge, and a surface, the edge defining at least a portion of a periphery of the surface, and the surface comprised at least in part by the visual display screen, a touch-sensitive input area, the touch-sensitive input area being across at least a portion of the surface area, a memory, and a processor within the housing and operatively coupled to the visual display screen, the memory and the touch-sensitive input area, wherein the processor comprises software for displaying an arcuate input bar, the arcuate input bar being an arc with a radius originating from a segment of the edge; prompting a user to provide an input by touching the arc with a finger at one or more points along a length of the arc, thereby providing input to the touch-sensitive input area; detecting the input to the touch-sensitive input area, including detecting a position along the arc of the input to the touch-sensitive input area; detecting a termination of the input to the touch-sensitive input area; and recording, to the memory, the input to the touch-sensitive input area as a last location of the input to the touch-sensitive input area preceding the detecting of the termination of the input to the touch-sensitive input area.

A method, apparatus, non-transitory computer readable medium, and system for rapidly capturing user input are described. One or more embodiments of the method, apparatus, non-transitory computer readable medium, and system include displaying an arcuate input bar, the arcuate input bar being an arc with a radius originating from a segment of an edge defining at least a portion of a periphery of a surface of a housing, prompting a user to provide an input by touching the arc with a finger at one or more points along a length of the arc, thereby providing input to a touch-sensitive input area of a visual display screen, detecting the input to the touch-sensitive input area, including detecting a position along the arc of the input to the touch-sensitive input area, detecting a termination of the input to the touch-sensitive input area, and recording the input to the touch-sensitive input area as a last location of the input to the touch-sensitive input area preceding the detecting of the termination of the input to the touch-sensitive input area.

An apparatus, system, and method for rapidly capturing user input are described. One or more embodiments of the apparatus, system, and method include a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and measuring a time between the prompting and the detecting of the termination, where recording the input to the touch-sensitive input area further comprises recording the time.

A method, apparatus, non-transitory computer readable medium, and system for rapidly capturing user input are described. One or more embodiments of the method, apparatus, non-transitory computer readable medium, and system include displaying an input bar, prompting a user to provide an input by touching the input bar with a finger at one or more points along a length of the input bar, thereby providing input to a touch-sensitive input area of a visual display screen, detecting the input to the touch-sensitive input area, including detecting a position along the input bar of the input to the touch-sensitive input area, detecting a termination of the input to the touch-sensitive input area, recording the input to the touch-sensitive input area as a last location of the input to the touch-sensitive input area preceding the detecting of the termination of the input to the touch-sensitive input area, and measuring a time between the prompting and the detecting of the termination, wherein recording to the memory the input to the touch-sensitive input area further comprises recording the time.

An apparatus, system, and method for rapidly capturing user input are described. One or more embodiments of the apparatus, system, and method include a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and detecting the input to the touch-sensitive input area, including detecting a degree of force applied for the input, wherein recording the input to the touch-sensitive input area further comprises recording the degree of force.

A method, apparatus, non-transitory computer readable medium, and system for rapidly capturing user input are described. One or more embodiments of the method, apparatus, non-transitory computer readable medium, and system include displaying an input bar, prompting a user to provide an input by touching the input bar with a finger at one or more points along a length of the input bar, thereby providing input to a touch-sensitive input area of a visual display screen, detecting the input to the touch-sensitive input area, including detecting a position along the input bar of the input to the touch-sensitive input area, detecting a termination of the input to the touch-sensitive input area, recording, to memory, the input to the touch-sensitive input area as a last location of the input to the touch-sensitive input area preceding the detecting of the termination of the input to the touch-sensitive input area, and detecting the input to the touch-sensitive input area, including detecting a degree of force applied for the input, wherein recording the input to the touch-sensitive input area further comprises recording the degree of force.

An apparatus, system, and method for rapidly capturing user input are described. One or more embodiments of the apparatus, system, and method include a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and detecting the input to the touch-sensitive input area, including detecting a pattern of movements of the finger preceding the last location, wherein recording the input to the touch-sensitive input area further comprises recording the pattern of movements.

A method, apparatus, non-transitory computer readable medium, and system for rapidly capturing user input are described. One or more embodiments of the method, apparatus, non-transitory computer readable medium, and system include displaying an input bar, prompting a user to provide an input by touching the input bar with a finger at one or more points along a length of the input bar, thereby providing an input to a touch-sensitive input area of a visual display screen, detecting the input to the touch-sensitive input area, including detecting a position along the input bar of the input to the touch-sensitive input area, detecting a termination of the input to the touch-sensitive input area, recording to the memory the input to the touch-sensitive input area as a last location of the input to the touch-sensitive input area preceding the detecting of the termination of the input to the touch-sensitive input area, and detecting the input to the touch-sensitive input area, including detecting a pattern of movements of the finger preceding the last location, wherein recording the input to the touch-sensitive input area further comprises recording the pattern of movements.

An apparatus, system, and method for rapidly capturing user input are described. One or more embodiments of the apparatus, system, and method include a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and detecting the input to the touch-sensitive input area, including detecting a speed of movement of the finger preceding the last location, wherein recording the input to the touch-sensitive input area further comprises recording the speed of movement of the finger preceding the last location.

A method, apparatus, non-transitory computer readable medium, and system for rapidly capturing user input are described. One or more embodiments of the method, apparatus, non-transitory computer readable medium, and system include displaying an input bar, prompting a user to provide an input by touching the input bar with a finger at one or more points along a length of the input bar, thereby providing an input to a touch-sensitive input area of a visual display screen, detecting the input to the touch-sensitive input area, including detecting a position along the input bar of the input to the touch-sensitive input area, detecting a termination of the input to the touch-sensitive input area, recording the input to the touch-sensitive input area as a last location of the input to the touch-sensitive input area preceding the detecting of the termination of the input to the touch-sensitive input area, and detecting the input to the touch-sensitive input area, including detecting a speed of movement of the finger preceding the last location, wherein recording the input to the touch-sensitive input area further comprises recording the speed of movement of the finger preceding the last location.

An apparatus, system, and method for rapidly capturing user input are described. One or more embodiments of the apparatus, system, and method include a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and detecting the input to the touch-sensitive input area, including detecting a speed of movement of the finger preceding the last location, wherein recording the input to the touch-sensitive input area further comprises recording the speed of movement of the finger preceding the last location.

A method, apparatus, non-transitory computer readable medium, and system for rapidly capturing user input are described. One or more embodiments of the method, apparatus, non-transitory computer readable medium, and system include displaying an input bar, prompting a user to provide an input by touching the input bar with a finger at one or more points along a length of the input bar, thereby providing an input to a touch-sensitive input area of a visual display screen, detecting the input to the touch-sensitive input area, including detecting a position along the input bar of the input to the touch-sensitive input area, detecting a termination of the input to the touch-sensitive input area, recording the input to the touch-sensitive input area as a last location of the input to the touch-sensitive input area preceding the detecting of the termination of the input to the touch-sensitive input area, and detecting a speed of movement of the finger preceding the last location, wherein recording the input to the touch-sensitive input area further comprises recording the speed of movement of the finger preceding the last location.

An apparatus, system, and method for rapidly capturing user input are described. One or more embodiments of the apparatus, system, and method include a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for performing the following steps: displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and measuring a time between initiation of the detecting of the input to the touch-sensitive input area and the detecting of the termination, wherein recording the input to the touch-sensitive input area further comprises recording the time.

A method, apparatus, non-transitory computer readable medium, and system for rapidly capturing user input are described. One or more embodiments of the method, apparatus, non-transitory computer readable medium, and system include displaying an input bar, prompting a user to provide an input by touching the input bar with a finger at one or more points along a length of the input bar, thereby providing an input to a touch-sensitive input area of a visual display screen, detecting the input to the touch-sensitive input area, including detecting a position along the input bar of the input to the touch-sensitive input area, detecting a termination of the input to the touch-sensitive input area, recording the input to the touch-sensitive input area as a last location of the input to the touch-sensitive input area preceding the detecting of the termination of the input to the touch-sensitive input area, and measuring a time between initiation of the detecting of the input to the touch-sensitive input area and the detecting of the termination, wherein recording the input to the touch-sensitive input area further comprises recording the time.

An apparatus, system, and method for rapidly capturing user input are described. One or more embodiments of the apparatus, system, and method include a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and detecting the input to the touch-sensitive input area, including detecting variations in speed of movements of the finger preceding the last location, wherein the recording the input to the touch-sensitive input area further comprises recording the variations in speed of movements.

A method, apparatus, non-transitory computer readable medium, and system for rapidly capturing user input are described. One or more embodiments of the method, apparatus, non-transitory computer readable medium, and system include displaying an input bar, prompting a user to provide an input by touching the input bar with a finger at one or more points along a length of the input bar, thereby providing an input to a touch-sensitive input area of a visual display screen, detecting the input to the touch-sensitive input area, including detecting a position along the input bar of the input to the touch-sensitive input area, detecting a termination of the input to the touch-sensitive input area, recording the input to the touch-sensitive input area as a last location of the input to the touch-sensitive input area preceding the detecting of the termination of the input to the touch-sensitive input area, and detecting the input to the touch-sensitive input area, including detecting variations in speed of movements of the finger preceding the last location, wherein the recording the input to the touch-sensitive input area further comprises recording the variations in speed of movements.

An apparatus, system, and method for rapidly capturing user input are described. One or more embodiments of the apparatus, system, and method include a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and detecting the input to the touch-sensitive input area, including detecting a pattern of movements of the finger preceding the last location, wherein recording the input to the touch-sensitive input area further comprises recording the pattern of movements.

A method, apparatus, non-transitory computer readable medium, and system for rapidly capturing user input are described. One or more embodiments of the method, apparatus, non-transitory computer readable medium, and system include displaying an input bar, prompting a user to provide an input by touching the input bar with a finger at one or more points along a length of the input bar, thereby providing an input to a touch-sensitive input area of a visual display screen, detecting the input to the touch-sensitive input area, including detecting a position along the input bar of the input to the touch-sensitive input area, detecting a termination of the input to the touch-sensitive input area, recording to the memory the input to the touch-sensitive input area as a last location of the input to the touch-sensitive input area preceding the detecting of the termination of the input to the touch-sensitive input area, and detecting the input to the touch-sensitive input area, including detecting a pattern of movements of the finger preceding the last location, wherein recording the input to the touch-sensitive input area further comprises recording the pattern of movements.

A method, apparatus, non-transitory computer readable medium, and system for rapidly capturing user input are described. One or more embodiments of the method, apparatus, non-transitory computer readable medium, and system include displaying an input bar, prompting a user to provide an input by touching the input bar with a finger at one or more points along a length of the input bar, thereby providing an input to a touch-sensitive input area of a visual display screen, detecting the input to the touch-sensitive input area, including detecting a position along the input bar of the input to the touch-sensitive input area, detecting a termination of the input to the touch-sensitive input area, recording to the memory the input to the touch-sensitive input area as a last location of the input to the touch-sensitive input area preceding the detecting of the termination of the input to the touch-sensitive input area, and detecting the input to the touch-sensitive input area, including detecting a pause in movement of the finger preceding the last location, wherein recording the input to the touch-sensitive input area further comprises recording the pause in movement.

An apparatus, system, and method for rapidly capturing user input are described. One or more embodiments of the apparatus, system, and method include a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and detecting the input to the touch-sensitive input area, including detecting a pause in movement of the finger preceding the last location, wherein recording the input to the touch-sensitive input area further comprises recording the pause in movement.

DETAILED DESCRIPTION

Figure 1:
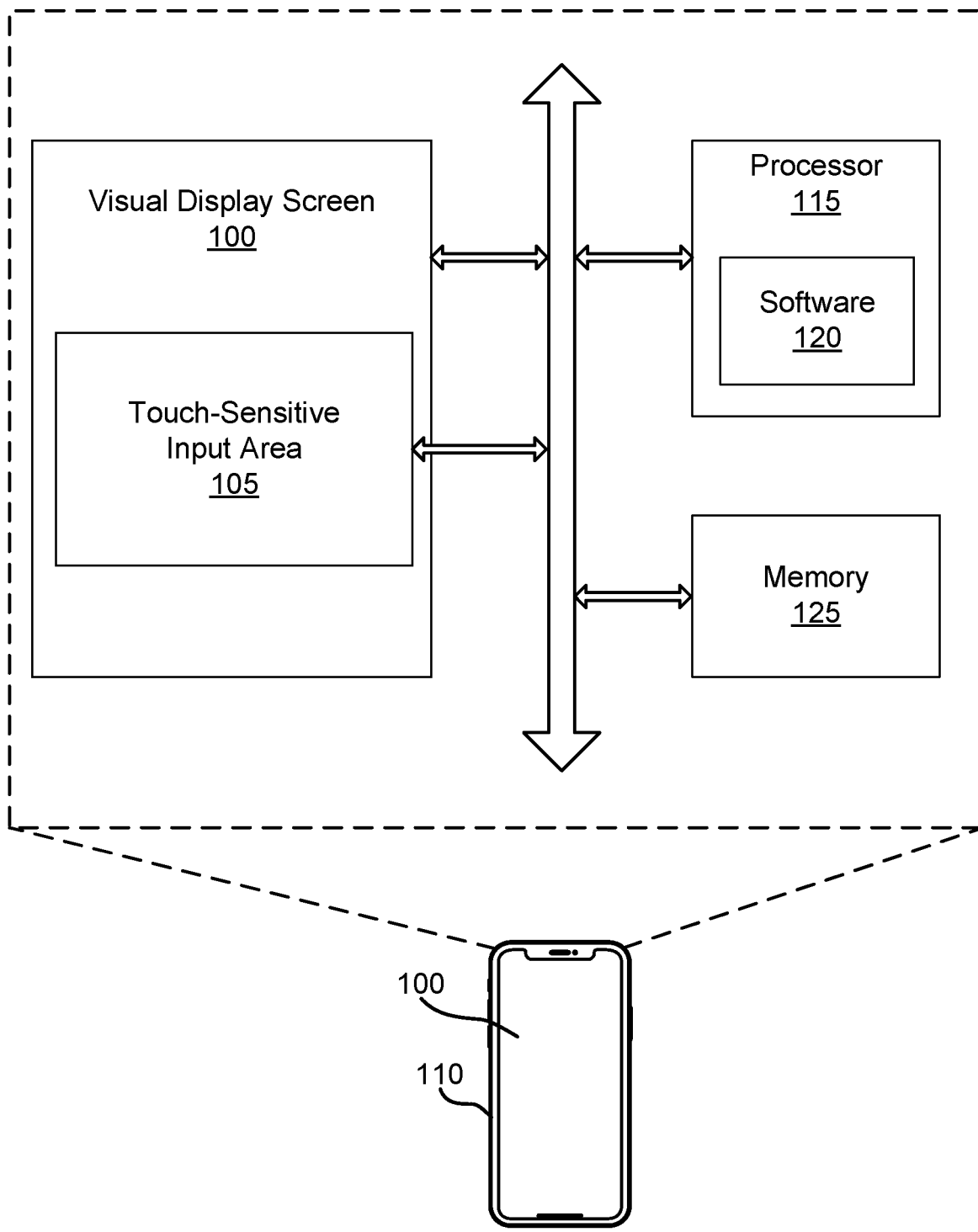
FIG. 1 shows an example of a system for rapidly capturing user input according to aspects of the present disclosure.

The following description is not to be taken in a limiting sense, but is made merely for the purpose of describing the general principles of exemplary embodiments. The scope of the invention should be determined with reference to the claims.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art will recognize, however, that the invention can be practiced without one or more of the specific details, or with other methods, components, materials, and so forth. In other instances, well-known structures, materials, or operations are not shown or described in detail to avoid obscuring aspects of the invention.

The present disclosure describes systems and methods for rapidly capturing user input. Some embodiments of the present disclosure may rapidly capture user input for psychometric analysis applications. For example, a Likert scale may be used for examining responses in survey-based research. A Likert scale is used to capture the intensity of feelings of a respondent for a given item or question and therefore, can be applied to multiple domains including psychology and social sciences, business and marketing, etc. Likert scales use questions that are correlated, which provides consistency and captures the complete discipline. Additionally, Likert scales may be used as ordinal scales while still including information resulting from bias in the analysis. A scaling system may use questionnaire responses over a set of individual items (e.g., respondent input prompts) to understand the feeling of the respondents. In some cases, a Likert scale may use several constituent items where each item includes a visual analogue scale to obtain the responses by a subject.

In various embodiments, the present disclosure can be applied to a range of possible question and answer scenarios, e.g. how much a user liked a book, how a user feels about their relationship, how the user would rate a product or experience.

According to techniques described herein, a visual display screen may prompt user (e.g., respondent) input (e.g., via an input prompt, question, statement, etc.). The visual display screen may capture user input using touch-sensitive input area. The touch-sensitive input area may include an input bar and an input position (e.g., a slider). A user may control the input position (e.g., via a finger of the user) along the input bar, such that user input may be captured, determined, recorded, etc., by the user input capture system.

Accordingly, user input may be more rapidly captured, and user input may be easily recognizable and understood by the user providing the user input (e.g., via visualization of a slider along an input bar, via visualization of an input indicator in addition to visualization of the slider along the input bar, etc.).

FIG. 1 shows an example of a system for rapidly capturing user input according to aspects of the present disclosure. The example shown includes visual display screen 100 and housing 110.

In some examples, a system for rapidly capturing user input may include a user device. A user device may be a personal computer, laptop computer, mainframe computer, palmtop computer, personal assistant, mobile device, or any other suitable processing apparatus. In some embodiments the user device is a smartphone, or tablet computing device. In some examples, the user device includes software 120 that prompts and captures user input, incorporates an event argument extraction or a question answering application (e.g., a dialogue system), etc.

A display (e.g., a visual display screen 100) may comprise a conventional monitor, a monitor coupled with an integrated display, an integrated display (e.g., an LCD display), or other means for viewing associated data or processing information.

A user interface (e.g., touch-sensitive input area 105) may enable a user to interact with a device. In some embodiments, the user interface may include an audio device, such as an external speaker system, an external display device such as a display screen, or an input device (e.g., remote control device interfaced with the user interface directly or through an IO controller module). In some cases, a user interface may be a graphical user interface (GUI).

An input device may be a computer mouse, keyboards, keypads, trackballs, and voice recognition devices. An input component may include any combination of devices that allow users to input information into a computing device, such as buttons, a keyboard, switches, and/or dials. In addition, the input component may include a touch-screen digitizer overlaid onto the display that can sense touch and interact with the display. For example, as described herein, an input device may include a touch-sensitive input area 105 that a user may interface with using a finger.

A processor 115 is an intelligent hardware device, (e.g., a general-purpose processing component, a digital signal processor (DSP), a central processing unit (CPU), a graphics processing unit (GPU), a microcontroller, an application specific integrated circuit (ASIC), a field programmable gate array (FPGA), a programmable logic device, a discrete gate or transistor logic component, a discrete hardware component, or any combination thereof). In some cases, the processor 115 is configured to operate a memory 125 array using a memory 125 controller. In other cases, a memory 125 controller is integrated into the processor 115. In some cases, the processor 115 is configured to execute computer-readable instructions stored in a memory 125 to perform various functions. In some embodiments, a processor 115 includes special purpose components for modem processing, baseband processing, digital signal processing, or transmission processing.

Software 120 may include code to implement aspects of the present disclosure. Software 120 may be stored in a non-transitory computer-readable medium such as system memory 125 or other memory 125. In some cases, the software 120 may not be directly executable by the processor 115 but may cause a computer (e.g., when compiled and executed) to perform functions described herein.

Examples of a memory 125 device include random access memory (RAM), read-only memory (ROM), or a hard disk. Examples of memory 125 devices include solid state memory and a hard disk drive. In some examples, memory 125 is used to store computer-readable, computer-executable software 120 including instructions that, when executed, cause a processor 115 to perform various functions described herein. In some cases, the memory 125 contains, among other things, a basic input/output system (BIOS) which controls basic hardware or software 120 operation such as the interaction with peripheral components or devices. In some cases, a memory 125 controller operates memory 125 cells. For example, the memory 125 controller can include a row decoder, column decoder, or both. In some cases, memory 125 cells within a memory 125 store information in the form of a logical state.

Some systems described herein may implement techniques for using computers to interpret user input. In some cases, such tasks may involve assigning annotation data such as grammatical information to user input. In some examples, different classes of machine-learning algorithms may be applied to received user input. These algorithms may take a set of features generated from the user input. Some algorithms, such as decision trees, may utilize hard if-then rules (e.g., to determine subsequent user input prompts to be displayed in response to received user input). Some systems may use neural networks or statistical models to make soft, probabilistic decisions (e.g., regarding subsequent user prompts, determinations made from user inputs, user analysis or user diagnosis based on received user input, etc.).

According to some embodiments, visual display screen 100 may have a surface area. According to some embodiments, visual display screen 100 displays an arcuate input bar, the arcuate input bar being an arc with a radius originating from a segment of an edge defining at least a portion of a periphery of a surface of a housing 110. In some examples, visual display screen 100 prompts a user to provide an input by touching the arc with a finger (e.g., the user's thumb) at one or more points along a length of the arc, thereby providing input to a touch-sensitive input area 105 of a visual display screen 100. In some embodiments, a base of the user's thumb is placed against the segment of the edge as the user sweeps a tip of the user's thumb along the arc, touching the arc with the tip of the thumb to provide the input while allowing the user to secure the visual display screen 100 (which may be a component of a smartphone or mobile device) between the base of the user's thumb and to the tips of the user's other fingers, which are wrapped around a back side of the visual display screen 100 so that the tips of the user's other fingers are able to reach another segment of another edge of the visual display screen 100.

According to some embodiments, visual display screen 100 displays an input bar. In some examples, visual display screen 100 prompts a user to provide an input by touching the input bar with a finger at one or more points along a length of the input bar, thereby providing input to a touch-sensitive input area 105 of a visual display screen 100.

In various embodiments, the input bar of the present disclosure can be a linear slider input bar, or any other shape suitable in a particular application of the present disclosure.

Visual display screen 100 is an example of, or includes aspects of, the corresponding element described with reference to FIGS. 2, 4, 5, 7, and 8. In one embodiment, visual display screen 100 includes touch-sensitive input area 105.

According to some embodiments, touch-sensitive input area 105 is, the touch-sensitive input area 105 being across at least a portion of the surface area. According to some embodiments, touch-sensitive input area 105 detects the input to the touch-sensitive input area 105, including detecting a position along the arc of the input to the touch-sensitive input area 105. In some examples, touch-sensitive input area 105 detects a termination of the input to the touch-sensitive input area 105.

Touch-sensitive input area 105 is an example of, or includes aspects of, the corresponding element described with reference to FIGS. 2, 4, 5, 7, and 8.

According to some embodiments, housing 110 is having an edge, and a surface, the edge defining at least a portion of a periphery of the surface, and the surface comprised at least in part by the visual display screen 100. Housing 110 is an example of, or includes aspects of, the corresponding element described with reference to FIGS. 2, 4, 5, 7, and 8. In one embodiment, housing 110 includes processor 115 and memory 125.

According to some embodiments, processor 115 is within the housing 110 and operatively coupled to the visual display screen 100, the memory 125 and the touch-sensitive input area 105, wherein the processor 115 comprises software 120 for displaying an arcuate input bar, the arcuate input bar being an arc with a radius originating from a segment of the edge. The processor 115 comprises software 120 for prompting a user to provide an input by touching the arc with a finger at one or more points along a length of the arc, thereby providing input to the touch-sensitive input area 105. The processor 115 comprises software 120 for detecting the input to the touch-sensitive input area 105, including detecting a position along the arc of the input to the touch-sensitive input area 105. The processor 115 comprises software 120 for detecting a termination of the input to the touch-sensitive input area 105, and recording, to the memory 125, the input to the touch-sensitive input area 105 as a last location of the input to the touch-sensitive input area 105 preceding the detecting of the termination of the input to the touch-sensitive input area 105.

In some examples, the software 120 may include software 120 for displaying a cursor feature along the arc at the position along the arc of the input to the touch-sensitive input area 105. In some examples, the software 120 may include software 120 for displaying at least one target along the arc. In some examples, the detecting of the input to the touch-sensitive input area 105 further includes detecting the position along the arc of the input to the touch-sensitive input area 105 when the position corresponds to at least one target along the arc. In some examples, the software 120 may include software 120 for displaying a response indicia separate from the arcuate input bar and varying the response indicia as a function of the position along the arc of the input to the touch-sensitive input area 105. In some examples, the software 120 may include software 120 for displaying a set of targets along the arc.

In some examples, the software 120 may include software 120 for measuring a time between the prompting and the detecting of the termination, and where recording the input to the touch-sensitive input area 105 further includes recording the time. In some examples, the software 120 may include software 120 for detecting the input to the touch-sensitive input area 105, including detecting a degree of force applied for the input, and where recording the input to the touch-sensitive input area 105 further includes recording the degree of force. In some examples, the software 120 may include software 120 for detecting the input to the touch-sensitive input area 105, including detecting a pattern of movements of the finger preceding the last location, and where recording the input to the touch-sensitive input area 105 further includes recording the pattern of movements.

In some examples, the software 120 may include software 120 for detecting the input to the touch-sensitive input area 105, including detecting a speed of movement of the finger preceding the last location, and where recording the input to the touch-sensitive input area 105 further includes recording the speed of movement. In some examples, the software 120 may include software 120 for automatically prompting, in response to the detecting of the termination of the input to the touch-sensitive input area 105, the user to provide additional input by touching the arc with the finger at one or more points along the length of the arc, thereby providing input to the touch-sensitive input area 105.

In some examples, the displaying of the arcuate input bar includes displaying the arcuate input bar in a first color, and changing, in response to the detecting of the input to the touch-sensitive input area 105, the first color to a second color. In some examples, the displaying of the arcuate input bar includes changing, in response to the detecting of the termination of the input to the touch-sensitive input area 105, the second color to the first color. In some examples, the displaying of the arcuate input bar includes displaying the arcuate input bar in a first color, and displaying the arcuate input bar further includes changing, in response to the detecting of the termination of the input to the touch-sensitive input area 105, the first color to a second color.

In some examples, the processor 115 comprises software 120 for measuring a time between the prompting and the detecting of the termination, where recording the input to the touch-sensitive input area 105 further comprises recording the time. According to some embodiments, processor 115 measures a time between the prompting and the detecting of the termination, where recording to the memory 125 the input to the touch-sensitive input area 105 further includes recording the time.

In some examples, the processor 115 comprises software 120 for detecting the input to the touch-sensitive input area 105, including detecting a degree of force applied for the input, wherein recording the input to the touch-sensitive input area 105 further comprises recording the degree of force. According to some embodiments, processor 115 detects the input to the touch-sensitive input area 105, including detecting a degree of force applied for the input, where recording the input to the touch-sensitive input area 105 further includes recording the degree of force.

In some examples, the processor 115 comprises software 120 for detecting the input to the touch-sensitive input area 105, including detecting a pattern of movements of the finger preceding the last location, wherein recording the input to the touch-sensitive input area 105 further comprises recording the pattern of movements. According to some embodiments, processor 115 detects the input to the touch-sensitive input area 105, including detecting a pattern of movements of the finger preceding the last location, where recording the input to the touch-sensitive input area 105 further includes recording the pattern of movements.

In some examples, the processor 115 comprises software 120 for detecting the input to the touch-sensitive input area 105, including detecting a speed of movement of the finger preceding the last location, wherein recording the input to the touch-sensitive input area 105 further comprises recording the speed of movement of the finger preceding the last location. According to some embodiments, processor 115 detects the input to the touch-sensitive input area 105, including detecting a speed of movement of the finger preceding the last location, where recording the input to the touch-sensitive input area 105 further includes recording the speed of movement of the finger preceding the last location.

In some examples, the processor 115 comprises software 120 for measuring a time between initiation of the detecting of the input to the touch-sensitive input area 105 and the detecting of the termination, wherein recording the input to the touch-sensitive input area 105 further comprises recording the time. According to some embodiments, processor 115 measures a time between initiation of the detecting of the input to the touch-sensitive input area 105 and the detecting of the termination, where recording the input to the touch-sensitive input area 105 further includes recording the time.

In some examples, the processor 115 comprises software 120 for detecting the input to the touch-sensitive input area 105, including detecting variations in speed of movements of the finger preceding the last location, wherein the recording the input to the touch-sensitive input area 105 further comprises recording the variations in speed of movements. According to some embodiments, processor 115 detects the input to the touch-sensitive input area 105, including detecting variations in speed of movements of the finger preceding the last location, where the recording the input to the touch-sensitive input area 105 further includes recording the variations in speed of movements.

According to some embodiments, processor 115 detects the input to the touch-sensitive input area 105, including detecting a pause in movement of the finger preceding the last location, where recording the input to the touch-sensitive input area 105 further includes recording the pause in movement.

According to some embodiments, processor 115 is operatively coupled to the visual display screen 100, the memory 125 and the touch-sensitive input area 105, wherein the processor 115 comprises software 120 for displaying an input bar; prompting a user to provide an input by touching the input bar with a finger at one or more points along a length of the input bar, thereby providing input to the touch-sensitive input area 105. In some examples, the processor 115 comprises software 120 for detecting the input to the touch-sensitive input area 105, including detecting a position along the input bar of the input to the touch-sensitive input area 105. In some examples, the processor 115 comprises software 120 for detecting a termination of the input to the touch-sensitive input area 105, and recording, to the memory 125, the input to the touch-sensitive input area 105 as a last location of the input to the touch-sensitive input area 105 preceding the detecting of the termination of the input to the touch-sensitive input area 105.

In some examples, the processor 115 comprises software 120 for detecting the input to the touch-sensitive input area 105, including detecting a pause in movement of the finger preceding the last location. In some examples, recording the input to the touch-sensitive input area 105 further comprises recording the pause in movement. In some examples, the software 120 may include software 120 for displaying a cursor feature along the input bar at the position along the input bar of the input to the touch-sensitive input area 105. In some examples, the software 120 may include software 120 for displaying at least one target along the input bar. In some examples, the detecting of the input to the touch-sensitive input area 105 further includes detecting the position along the input bar of the input to the touch-sensitive input area 105 when the position corresponds to at least one target along the input bar.

In some examples, the software 120 may include software 120 for displaying a response indicia separate from the input bar and varying the response indicia as a function of the position along the input bar of the input to the touch-sensitive input area 105. In some examples, the software 120 may include software 120 for detecting the input to the touch-sensitive input area 105, including detecting a pattern of movements of the finger preceding the last location, where recording the input to the touch-sensitive input area 105 further includes recording the pattern of movements. In some examples, the software 120 may include software 120 for detecting the input to the touch-sensitive input area 105, including detecting a speed of movement of the finger preceding the last location, where recording the input to the touch-sensitive input area 105 further includes recording the speed of movement.

In some examples, the software 120 may include software 120 for automatically prompting, in response to the detecting of the termination of the input to the touch-sensitive input area 105, the user to provide additional input by touching the input bar with the finger at one or more points along the length of the input bar, thereby providing input to the touch-sensitive input area 105. In some examples, the displaying of the input bar includes displaying the input bar in a first color and changing, in response to the detecting of the input to the touch-sensitive input area 105, the first color to a second color. In some examples, the displaying of the input bar further includes changing, in response to the detecting of the termination of the input to the touch-sensitive input area 105, the second color to the first color. In some examples, the displaying of the input bar includes displaying the input bar in a first color and changing, in response to the detecting of the termination of the input to the touch-sensitive input area 105, the first color to a second color.

In some examples, the software 120 may include software 120 for displaying a set of targets along the input bar. In some examples, the detecting of the input to the touch-sensitive input area 105, where the detecting further includes detecting the position along the input bar of the input to the touch-sensitive input area 105 when the position corresponds to at least one target along the input bar. In some examples, the software 120 may include software 120 for detecting the input to the touch-sensitive input area 105, including detecting a variation of speed of movement of the finger preceding the last location, and where recording the input to the touch-sensitive input area 105 further includes recording the variation of speed of movement.

According to some embodiments, memory 125 records the input to the touch-sensitive input area 105 as a last location of the input to the touch-sensitive input area 105 preceding the detecting of the termination of the input to the touch-sensitive input area 105. According to some embodiments, memory 125 records, to memory 125, the input to the touch-sensitive input area 105 as a last location of the input to the touch-sensitive input area 105 preceding the detecting of the termination of the input to the touch-sensitive input area 105. According to some embodiments, memory 125 records to the memory 125 the input to the touch-sensitive input area 105 as a last location of the input to the touch-sensitive input area 105 preceding the detecting of the termination of the input to the touch-sensitive input area 105.

Figure 2:
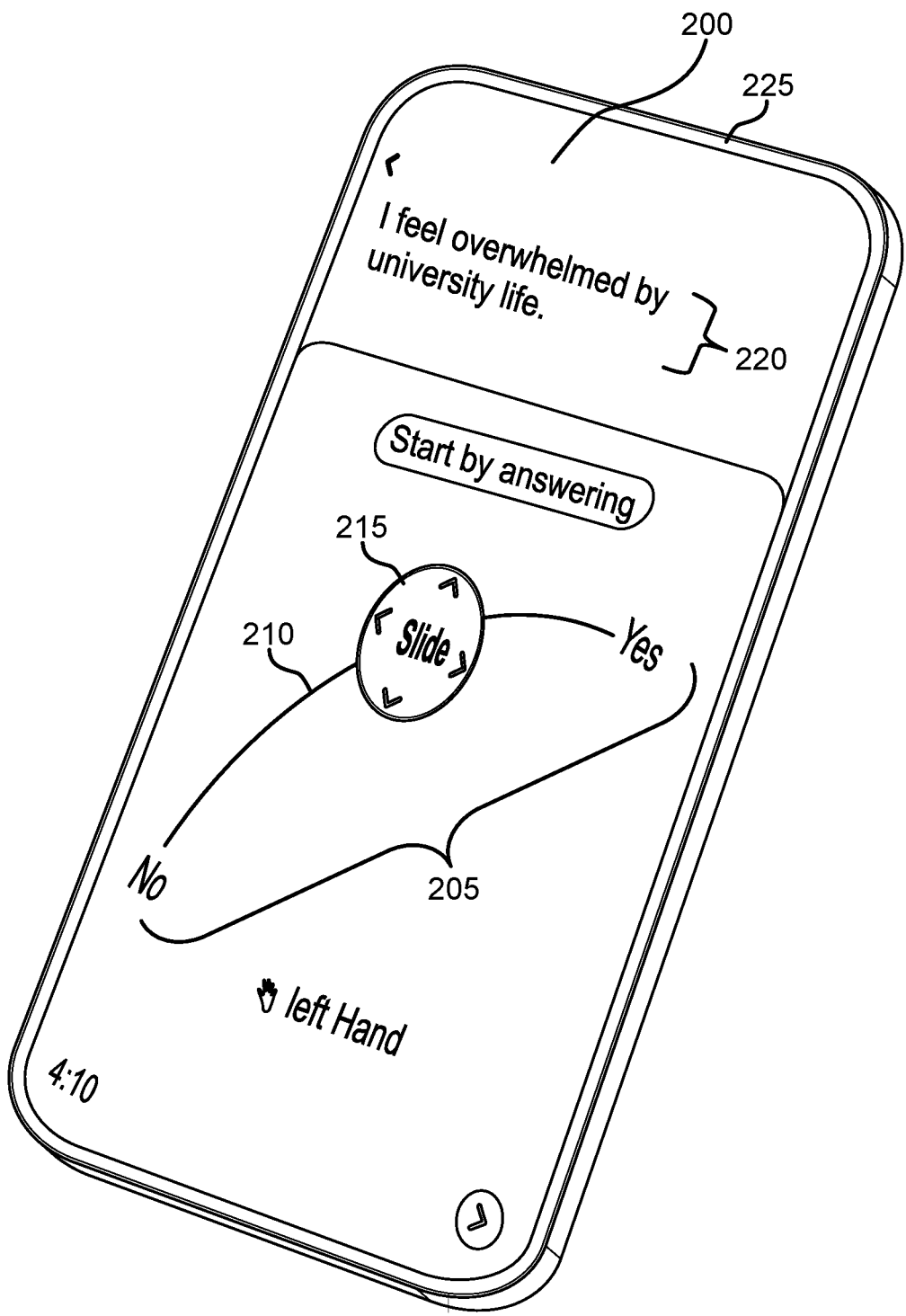
FIG. 2 shows an example of an example device for rapidly capturing user input according to aspects of the present disclosure.

FIG. 2 shows an example of an example device for rapidly capturing user input according to aspects of the present disclosure. According to some aspects of the present disclosure, FIG. 2 may illustrate an example device that may implement a system for rapidly capturing user input. The example shown includes visual display screen 200 and housing 225. For instance, visual display screen 200 may include input prompt 220, which may prompt input from a user (e.g., such as an answer to a question posed via input prompt 220) using touch-sensitive input area 205 of the visual display screen 200.

According to techniques described herein, a visual display screen may prompt user input (e.g., via input prompt 220) and may capture user input using touch-sensitive input area 205. The touch-sensitive input area 205 may include an input bar 210 and an input position 215. A user may control input position 215 (e.g., via a finger of the user) along the input bar 210 such that user input may be captured, determined, recorded, etc.

In the example of FIG. 2, an input prompt 220 may include the phrase "I feel overwhelmed by university life." The input bar 210 may indicate a range from "No" to "Yes," and a user may interface with touch-sensitive input area 205 (e.g., via a finger) and slide the input position 215 to indicate varying responses from "No" to "Yes."

For example, a system described herein (e.g., via a processor comprising software) may display an input bar 210 (e.g., an arcuate input bar 210). In some examples, the input bar 210 may include an arc with a radius originating from a segment of an edge of housing 225. The system may prompt a user to provide an input by touching the arc (e.g., with a finger) at one or more points (e.g., or input positions 215) along a length of the input bar 210 (e.g., along the length of the arc), thereby providing input to the touch-sensitive input area 205 based on the final input position 215 selected by the user.

Accordingly, the system may detect the input to the touch-sensitive input area 205, including detecting an input position 215 along the arc of the input to the touch-sensitive input area 205. For example, the system may detect a termination of the input to the touch-sensitive input area 205 (e.g., such as the input position 215 after a user finger is lifted from the touch-sensitive input area 205). The system may record (e.g., to memory) the input to the touch-sensitive input area 205 as a last location (e.g., or input position 215) of the input to the touch-sensitive input area 205 preceding the detecting of the termination of the input to the touch-sensitive input area 205. In some examples, a cursor feature (e.g., a "slide") may be displayed along the arc at the input position 215 along the arc of the input to the touch-sensitive input area 205.

Visual display screen 200 is an example of, or includes aspects of, the corresponding element described with reference to FIGS. 1, 4, 5, 7, and 8. In one embodiment, visual display screen 200 includes touch-sensitive input area 205 and input prompt 220. Touch-sensitive input area 205 is an example of, or includes aspects of, the corresponding element described with reference to FIGS. 1, 4, 5, 7, and 8. In one embodiment, touch-sensitive input area 205 includes input bar 210 and input position 215. Input bar 210 is an example of, or includes aspects of, the corresponding element described with reference to FIGS. 4, 5, 7, and 8. Input position 215 is an example of, or includes aspects of, the corresponding element described with reference to FIGS. 4, 5, 7, and 8. Input prompt 220 is an example of, or includes aspects of, the corresponding element described with reference to FIGS. 4, 5, 7, and 8.

Housing 225 is an example of, or includes aspects of, the corresponding element described with reference to FIGS. 1, 4, 5, 7, and 8.

In some examples, some systems for capturing user input described herein may implement one or more aspects of a Likert scale, which is a psychometric scale involved in research that employs questionnaires. A Likert scale may be used to scale responses in survey research. In some examples, a Likert-type scale may generally be referred to as a rating scale (e.g., or a Likert-type scale may be a type of rating scale).

A Likert scale may distinguish between a scale proper, which emerges from collective responses to a set of items (usually eight or more), and the format in which responses are scored along a range. The difference between a scale proper and the format of response scoring includes a distinction between the underlying phenomenon being investigated and the means of capturing variation that points to the underlying phenomenon.

When responding to a Likert item (e.g., input prompt 220), respondents (e.g., users) provide the level of agreement or disagreement on a symmetric agree-disagree scale for a series of statements. For instance, in the example of FIG. 2, users may respond to the input prompt 220 and provide the user's level of agreement or disagreement on a symmetric agree-disagree scale by adjusting input position 215 along the length of the input bar 210. Therefore, the range along the input bar 210 may capture the intensity of feelings of the respondents for a given input prompt 220. Likert scales may be applied in psychology and social sciences, statistics, business and marketing.

A scale may include or refer to the sum or average of questionnaire responses over the set of individual items or questions (e.g., over the set of input prompts 220). Likert scaling may assume distances between each choice (answer option) are equal. In some cases, a set of items that are correlated (i.e., show internal consistency) and capture the full domain under study (which requires less-than perfect correlations) are employed. Alternatively, items may be replications of each other (i.e., items are parallel instruments). By contrast, a test theory treats the difficulty of an individual item (the item response functions) as information to be incorporated in scaling items.

A Likert scale is a sum of responses on several Likert items (e.g., input prompts 220). In some cases, an individual item is referred to as being or having a scale because many Likert scales pair constituent Likert items with an instance of a visual analogue scale of that item (e.g., a horizontal line, on which the subject indicates a response by circling or checking tick-marks).

One or more embodiments of the present disclosure include an input prompt 220 (e.g., a Likert item) which may include a statement that a respondent is asked to evaluate by providing a quantitative value (e.g., an input position 215) on a subjective or objective dimension, with level of agreement or disagreement as the used dimension. Likert items exhibit symmetry and balance. Symmetry refers to equal numbers of positive and negative positions (e.g., along an input bar 210) where distances between positive and negative positions are bilaterally symmetric about the neutral or zero value (i.e., independent of the value being presented as a candidate). Balance in Likert items implies that the distance between candidate value is the same, such that quantitative comparisons, for example, averaging, are valid across items containing more than two candidate values. The format of a five-level Likert item, for example, may be strongly disagree, disagree, neither agree nor disagree, agree, and strongly agree.

Likert scaling is a bipolar scaling method, measuring positive or negative response to a statement. In some cases, an even-point scale is used where the option of neither agree nor disagree is not available. This is a forced choice method since the neutral option is removed. The neutral option is an easy option when a respondent is unsure. As a result, a true neutral option is questionable. The differences between the use of undecided and neutral as an option in a five-point Likert scale are insignificant.

In some examples, respondents may avoid using extreme response categories (i.e., central tendency bias). For instance, respondents may avoid providing input positions 215 at the extreme edges of the range along input bar 210. This is due to a desire to avoid being perceived as having extremist views (i.e., social desirability bias). The effect of central tendency bias may appear early in a test due to an expectation that questions which a subject has stronger views on may follow. As a result, on earlier questions the subject may make space for stronger responses later in the test. The expectation of stronger responses later in the test may create a bias such that the effects of the bias are not uniform throughout the test. Additionally, the bias may not be corrected through across-the-board normalization.

In some cases, respondents may agree with statements as presented (acquiescence bias). This effect is strong among persons, such as children, developmentally disabled persons, and the elderly or infirm, who are subjected to a culture of institutionalization that encourages and incentivizes eagerness to please. Alternatively, respondents may disagree with sentences as presented due to a defensive desire to avoid making erroneous statements. Respondents fear and/or avoid the resulting negative consequences if the answers are misinterpreted and/or taken out of context.

In some cases, respondents may provide answers that the respondents believe will be evaluated as indicating strength or lack of weakness or dysfunction (referred to as faking good). In some examples, a respondent may provide answers to a statement that the respondent believes will be evaluated as indicating weakness or presence of impairment or pathology (referred to as faking bad). Respondents may try to portray themselves or the associated organization based on the respondent's belief that the examiner or society will consider certain responses more favorable than the true beliefs. This is referred to as social desirability bias or the intersubjective version of objective faking good. Alternatively, respondents may try to portray themselves or the associated organization such that the respondent believes the examiner or society to consider less favorable than the true beliefs. This is referred to as norm defiance or the intersubjective version of objective faking bad.

One or more embodiments of the present disclosure provide a balanced keying scale with an equal number of positive and negative statements, and an equal number of positive and negative statements regarding each position or issue in question. The balanced keying scale can obviate acquiescence bias, since acquiescence on positively keyed items will balance acquiescence on negatively keyed items.

One or more embodiments of the present disclosure may analyze input prompts 220 (e.g., Likert items) separately or by creating a score for a group of Likert items using summation after the questionnaire is completed. Likert items may be considered as interval-level data, as ordered-categorical data or as ordinal data.

In some aspects, Likert scales or summative scales may be arbitrary. The value assigned to a Likert item has no objective numerical basis, in terms of measure theory or scale from which a distance metric can be determined. The value assigned to a Likert item may be determined by the researcher designing the survey, who decides the values based on a desired level of detail. Likert items are assigned progressive positive integer values. For example, a Likert scale may range from 2 to 10 with 3 or 5 being the most common. Furthermore, the progressive structure of the scale is such that the successive Likert item is treated as indicating an improved response than the preceding value. Alternatively, a reverse ordering of the Likert scale will change the numerical values assigned to the Likert items.

In some embodiments, the distance between successive item categories in Likert scales may be evaluated to check for equivalence. For example, in a five-point Likert item, the distance between categories 1 and 2 is the same as between categories 3 and 4. An equidistant presentation by the researcher provides for avoiding a bias in the analysis. In other cases, a four-point Likert item with categories poor, average, good, and very good may not have equidistant categories since there is one category (i.e., poor) that can receive a below-average rating. Equidistant categories in a four-point Likert item will bias any result in favor of a positive outcome. As a result, equidistant categories may not be interpreted alike by a researcher and respondent.

A Likert scale may present a symmetry of categories about a midpoint with clearly defined linguistic qualifiers. In symmetric scaling, equidistant attributes may be observed or inferred. A Likert scale may be similar to an interval-level measurement when a Likert scale is symmetric and equidistant. A Likert scale may approximate an interval-level measurement if well-presented. In some aspects, a Likert scale works similar to an ordinal scale and uses the distance between Likert items to capture useful information. The appropriate type of analysis may be dependent on the presentation of the Likert scale.

Notions of central tendency are applicable at the item level (i.e., responses often show a quasi-normal distribution). The validity of central tendency depends on the interval nature of the scale. The paired samples t-test is considered appropriate if interval nature is assumed for a comparison of two groups. In some cases, a statistical hypothesis test which incorporates zero differences and compares two samples to assess the mean ranks (e.g., Pratt modification to the Wilcoxon signed-rank test) is used if non-parametric tests are performed.

In some examples, responses to input prompts 220 (e.g., Likert questions) may be summed if the input prompts 220 (e.g., Likert questions) use the same Likert scale. A Likert scale is a defensible approximation to an interval scale, in which case the central limit theorem provides for treatment of the data as interval data measuring a latent variable. Parametric statistical tests such as the analysis of variance may be applied if the summed responses fulfill the central limit theorem assumptions. For instance, a cutoff for the approximation to be acceptable is eight items in the sum (minimum of four items).

To model binary Likert responses directly, binary Likert responses may be represented in a binomial form by summing agree and disagree responses separately. In some examples, statistical procedures (e.g., chi-squared, Cochran's Q test, or McNemar test) may be used after the transformation. Non-parametric tests (e.g., chi-squared test, Mann-Whitney test, Wilcoxon signed-rank test, or Kruskal-Wallis test) are used in the analysis of Likert scale data.

Alternatively, Likert scale responses (e.g., captured input positions 215) can be analyzed with a generalized regression model (e.g., an ordered probit model) preserving the ordering of responses without the assumption of an interval scale. The use of a regression model can prevent errors that arise when treating ordered ratings as interval-level measurements.

Consensus-based assessment (CBA) may be used to create an objective standard for Likert scales in domains where generally accepted or objective standards do not exist. Consensus-based assessment (CBA) may be used to refine or validate generally accepted standards.

In some examples, visualization (or plotting) of data may be used for data analysis and presentation. For instance, Likert rating data may be plotted using diverging stacked bar charts and comparing with other plotting styles. Additionally, Likert function may be used in a programming language for statistical computing and graphing (e.g., HH package for R).

In some examples, five response categories in a Likert scale may represent an interval level of measurement if the intervals between the scale points correspond to empirical observations in a metric sense. The criterion for interval level of measurement is met by a visual analogue scale. There may also be phenomena which question the ordinal scale level in Likert scales. For example, in a set of items A, B, C rated with a Likert scale, circular relations like A>B, B>C and C>A may exist which violates the axiom of transitivity for the ordinal scale.

Likert-type items perform close to scales that are perceived as equal intervals with large distortions of perceived distances between scale points. Likert-type items and other equal-appearing scales in questionnaires are robust to violations of the equal distance assumption for parametric statistical procedures and tests.

In some examples, Likert scale data may be used as a basis for interval level estimates on a continuum by applying a polytomous Rasch model, when data that fits the model is obtained. Additionally, the polytomous Rasch model tests the hypothesis that the statements reflect increasing levels of an attitude or trait. For example, application of the model indicates that the neutral category does not represent a level of attitude or trait between the disagree and agree categories.

One or more embodiments of the present disclosure may use Likert scaled items for Rasch measurement. The data to be used in Rasch measurement may be checked to fulfill the formal axioms of the model. The raw scores are statistics for the Rasch measures (e.g., if raw scores are accepted as valid, the Rasch measures are valid).

Figure 3B:
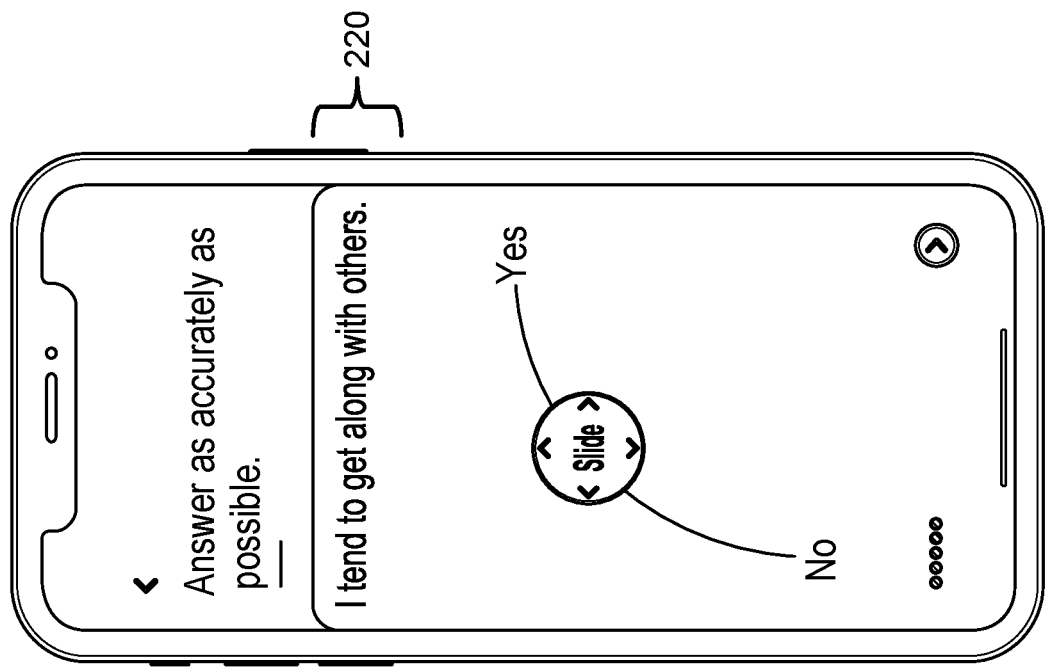
FIGS. 3A and 3B show example user input prompt displays according to aspects of the present disclosure.
Figure 3A:
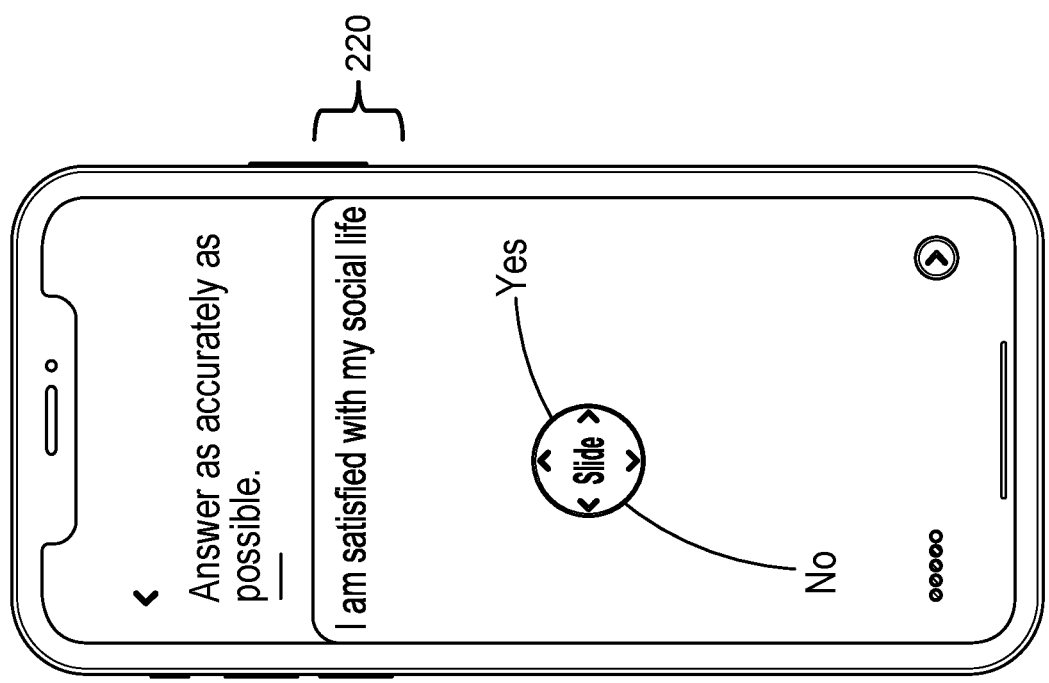

FIGS. 3A and 3B show example user input prompt displays 300 and 301, respectively, according to aspects of the present disclosure. User input prompt displays 300 and 301 may be examples of, or include aspects of, the corresponding element described with reference to FIG. 6. FIGS. 3A and 3B may illustrate examples of different input prompts 220 that may be displayed, where a system for rapidly capturing user input may be implemented according to techniques described herein.

For instance, FIG. 3A may illustrate example user input prompt display 300, where an input prompt 220 may include the phrase "I am satisfied with my social life." A user may use a slider (e.g., to adjust an input position along an input bar arc) to input a response to the input prompt 220. Accordingly, a user may input a response based on how satisfied a user is with the user's social life (e.g., ranging from "No" to "Yes").

FIG. 3B may illustrate example user input prompt display 301, where an input prompt 220 may include the phrase "I tend to get along with others." A user may use a slider (e.g., to adjust an input position along an input bar arc) to input a response to the input prompt 220. Accordingly, a user may input a response based on how well the user perceives they get along with others (e.g., ranging from "No" to "Yes").

As such, one or more aspects described herein may be implemented for various applications, various input prompts 220, etc. For example, the techniques described herein may be implemented to rapidly capture user input for various user input prompts 220 prompting any user input. Accordingly, user input may be more rapidly captured, and user input may be easily recognizable and understood by the user providing the user input (e.g., via visualization of the slider along an input bar, via visualization of the input indicator in addition to visualization of the slider along the input bar, etc.).

Figure 4B:
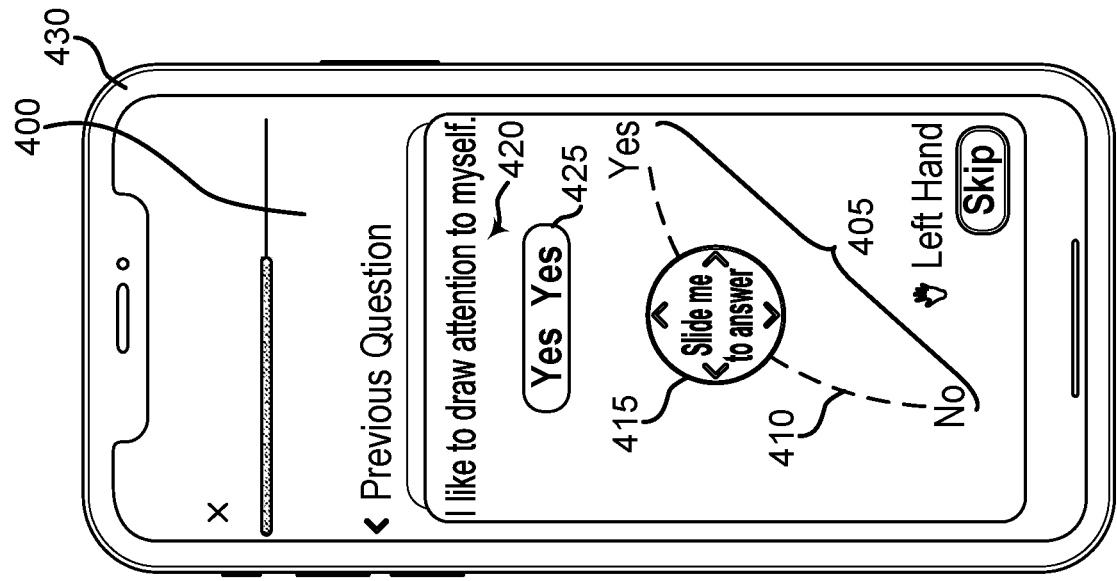
FIGS. 4A, 4B, and 5A-5C show examples of a system for rapidly capturing user input according to aspects of the present disclosure.
Figure 4A:
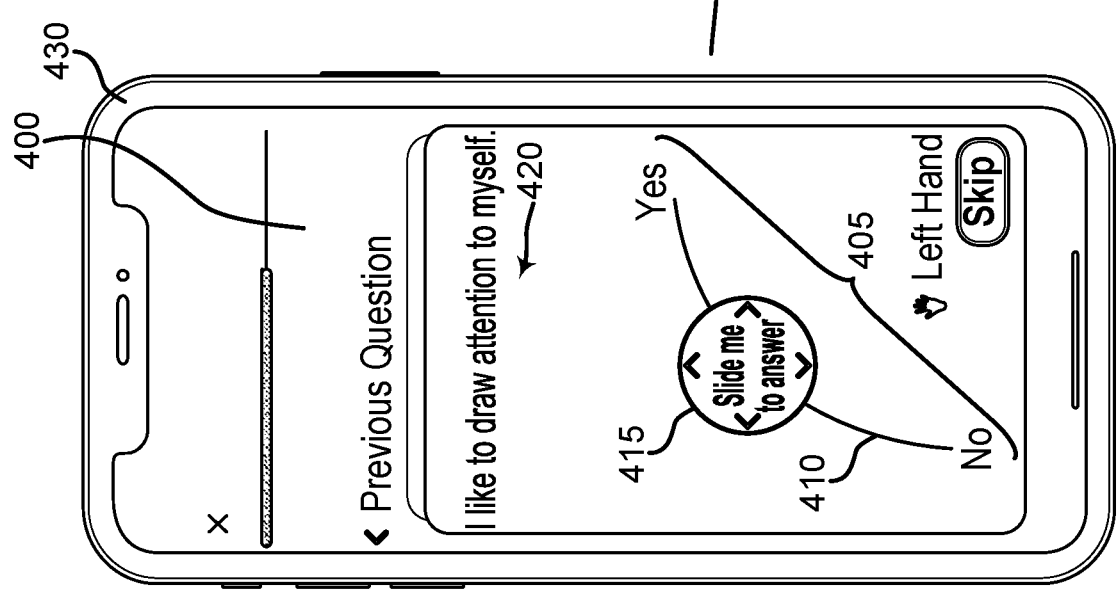

FIGS. 4A and 4B show an example of a system for rapidly capturing user input according to aspects of the present disclosure. The example shown includes visual display screen 400 and housing 430.

Visual display screen 400 is an example of, or includes aspects of, the corresponding element described with reference to FIGS. 1, 2, 5, 7, and 8. In one embodiment, visual display screen 400 includes touch-sensitive input area 405, input prompt 420, and input indicator 425. Touch-sensitive input area 405 is an example of, or includes aspects of, the corresponding element described with reference to FIGS. 1, 2, 5, 7, and 8. In one embodiment, touch-sensitive input area 405 includes input bar 410 and input position 415. Input bar 410 is an example of, or includes aspects of, the corresponding element described with reference to FIGS. 2, 5, 7, and 8. Input position 415 is an example of, or includes aspects of, the corresponding element described with reference to FIGS. 2, 5, 7, and 8.

Input prompt 420 is an example of, or includes aspects of, the corresponding element described with reference to FIGS. 2, 5, 7, and 8. Input indicator 425 is an example of, or includes aspects of, the corresponding element described with reference to FIGS. 5, 7, and 8.

Housing 430 is an example of, or includes aspects of, the corresponding element described with reference to FIGS. 1, 2, 5, 7, and 8.

FIGS. 4A and 4B may illustrate an example where an input bar 410 indicates when a touch-sensitive input area 405 is activated. For example, FIG. 4A may illustrate an example user input prompt display where the touch-sensitive input area 405 is not activated (e.g., where a user's finger is not activating touch-sensitive input area 405). FIG. 4B may illustrate an example user input prompt display where the touch-sensitive input area 405 is activated (e.g., where a user's finger is physically touching and activating touch-sensitive input area 405). For instance, FIG. 4B may illustrate an example user input prompt display after a user touches (e.g., activates) the example user input prompt display of FIG. 4B (e.g., via a user touching a slider along an input bar).

In other words, an input bar 410 may be displayed in a first manner (e.g., as shown in FIG. 4A) and may change in response to detecting user input to the touch-sensitive input area 405. For example, input bar 410 may change line thickness, line dash style, line color, etc., in response to detecting user input to the touch-sensitive input area 405. In some examples, user input to the touch-sensitive input area 405 may be detected when a user touches a slider (e.g., a target along the arc of input bar 410).

Generally, any aspect of the user input prompt display may be in a first state (e.g., a first line thickness, line dash style, line color, text font, text size, text color, etc.) prior to user activation and may change to a second state in response to detecting user input to the touch-sensitive input area 405. In some examples, the changing aspect that indicates user activation may include the input bar 410, the slider, the input prompt 420, an input indicator 425, etc.

In some examples, an input indicator 425 may appear in response to detecting user input to the touch-sensitive input area 405. As described in more detail herein (e.g., with reference to FIGS. 5A-5C), an input indicator 425 may further indicate input position 415 (e.g., via text indicative of a position of the slider along input bar 410).

Additionally or alternatively, some systems for rapidly capturing user input described herein may include haptic feedback indicative of whether user input to the touch-sensitive input area 405 is detected. Haptic feedback systems interact with a user's sense of touch by applying mechanical forces, vibrations, or motions. Haptic stimulation can be used to create or interact with virtual objects in a computer simulation, and to enhance the remote control of machines and devices. Haptic devices may incorporate tactile sensors that measure forces exerted by the user on the interface.

In some examples, any aspect of the user input prompt display described above may revert back from the second state (e.g., the state indicative of user input to the touch-sensitive input area 405) to the first state (e.g., the state indicative of no user input to the touch-sensitive input area 405) upon detection that the user input to the sensitive input area 405 has been terminated. For example, the input bar 410 may be changed, in response to the detecting of the termination of user input to the touch-sensitive input area 405, from a second color to a first color. In the example of FIGS. 4A and 4B, the input bar 410 may revert from the example of FIG. 4B to the example of FIG. 4A after detecting termination of user input to the touch-sensitive input area 405.

FIG. 5 shows an example of a system for rapidly capturing user input according to aspects of the present disclosure. The example shown includes visual display screen 500 and housing 530.

Visual display screen 500 is an example of, or includes aspects of, the corresponding element described with reference to FIGS. 1, 2, 4, 7, and 8. In one embodiment, visual display screen 500 includes touch-sensitive input area 505, input prompt 520, and input indicator 525. Touch-sensitive input area 505 is an example of, or includes aspects of, the corresponding element described with reference to FIGS. 1, 2, 4, 7, and 8. In one embodiment, touch-sensitive input area 505 includes input bar 510 and input position 515. Input bar 510 is an example of, or includes aspects of, the corresponding element described with reference to FIGS. 2, 4, 7, and 8. Input position 515 is an example of, or includes aspects of, the corresponding element described with reference to FIGS. 2, 4, 7, and 8.

Input prompt 520 is an example of, or includes aspects of, the corresponding element described with reference to FIGS. 2, 4, 7, and 8. Input indicator 525 is an example of, or includes aspects of, the corresponding element described with reference to FIGS. 4, 7, and 8.

Housing 530 is an example of, or includes aspects of, the corresponding element described with reference to FIGS. 1, 2, 4, 7, and 8.

Figure 5C:
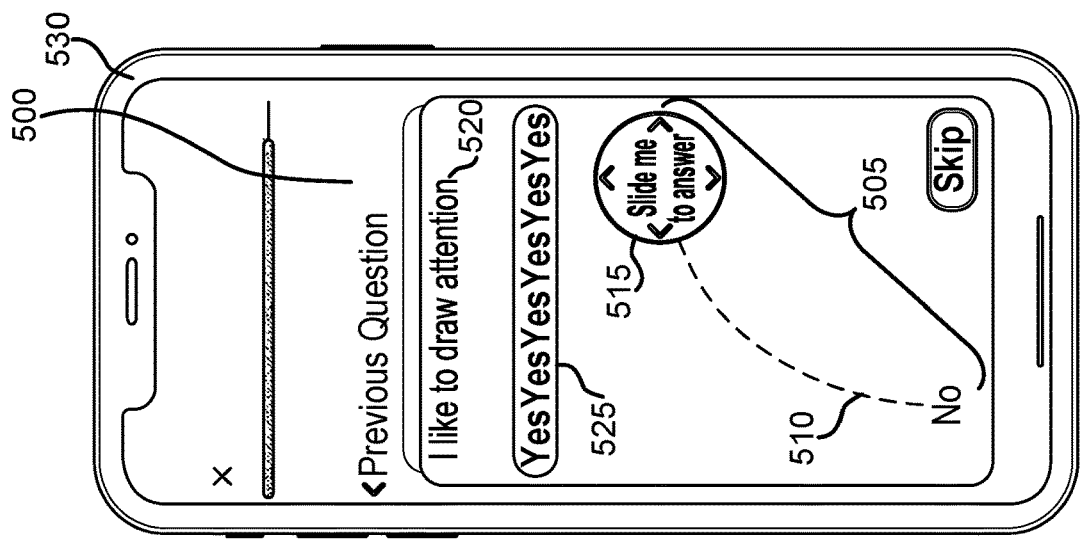
Figure 5B:
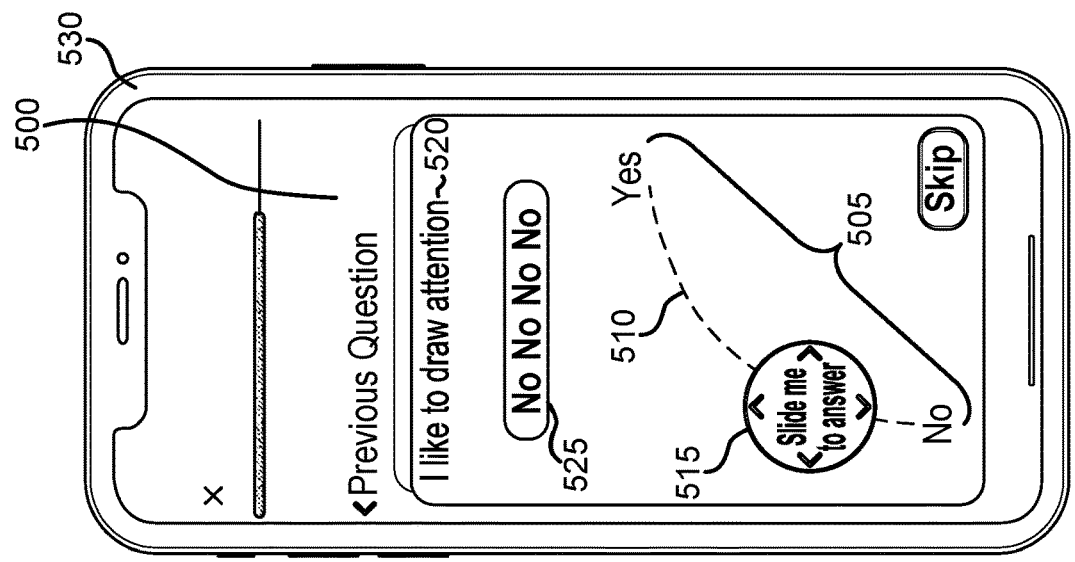
Figure 5A:
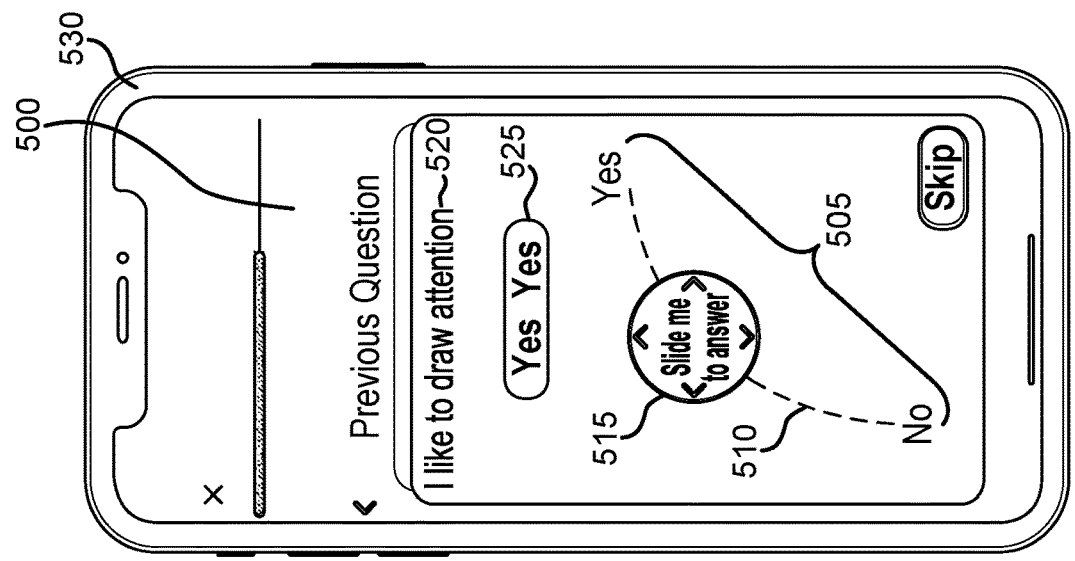

FIGS. 5A-5C may illustrate an example where a slider may be used to adjust an input position 515 along input bar 510, where the input position 515 prior to termination of user input may correspond to the captured user input. FIGS. 5A-5C show an example where a user input prompt 520 prompts user input to the phrase "I like to draw attention," (e.g., prompting user input regarding whether the user likes to draw attention to oneself).

Further, FIGS. 5A-5C illustrate an input indicator 525 providing additional visualization feedback corresponding to the input position 515 being controlled by a user. For example, FIG. 5A shows input position 515 slightly past the middle of the length along the arc of input bar 510. In FIG. 5A, the input indicator 525 displays "Yes Yes." FIG. 5B shows input position 515 towards the bottom end (e.g., the "No" end) of the length along the arc of input bar 510. In FIG. 5B, the input indicator 525 displays "No No No No." FIG. 5C shows input position 515 at the top end (e.g., the "Yes" end) of the length along the arc of input bar 510. In FIG. 5C, the input indicator 525 displays "Yes Yes Yes Yes Yes Yes." In the examples shown in FIGS. 5A-5C a degree of the user's conviction or confidence in their response is indicated by the user selecting an input position with more (or less) instances of the word "Yes" (i.e., more instances of the word "Yes" indicates more (or less) conviction or confidence) or "No" (i.e., more (or less) instances of the word "No" indicates more (or less) convistion or confidence) in the "Yes" or "No" response.

Accordingly, in some implementations, the input indicator 525 may provide a visual indication of the user input (e.g., of the input position 515 along input bar 510). As such, user's may effectively visualize their responses to input prompt 520.

Figure 6B:
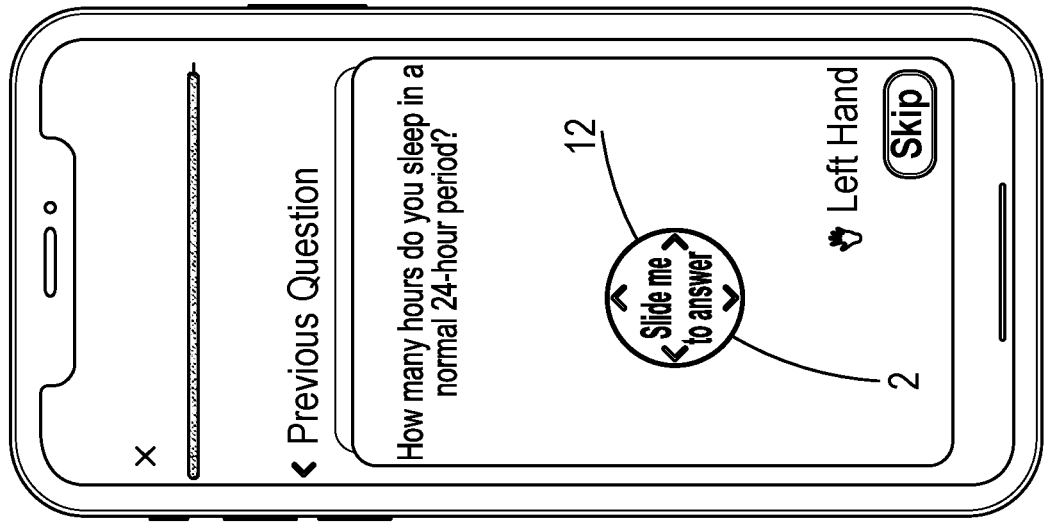
FIGS. 6A and 6B show example user input prompt displays according to aspects of the present disclosure.
Figure 6A:
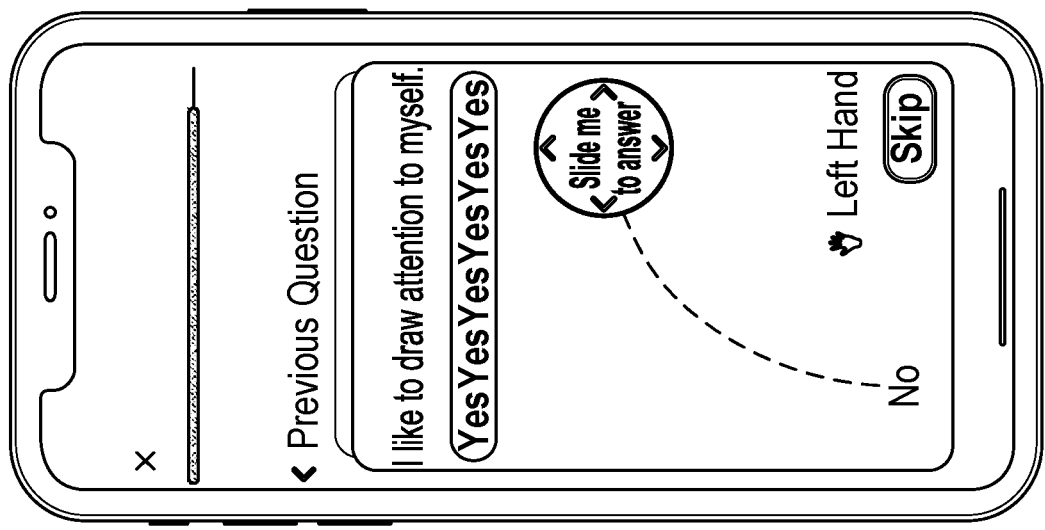

FIGS. 6A and 6B show example user input prompt displays 600 and 601 according to aspects of the present disclosure. User input prompt display 600 is an example of, or includes aspects of, the corresponding element described with reference to FIG. 3. For example, FIGS. 6A and 6B may illustrate aspects of some systems described herein where a new user input prompt may be displayed once user input is captured for a user input prompt. For instance, FIG. 6A shows an example where user input is captured for the input prompt "I like to draw attention to myself." After the user input is captured (e.g., after the user releases the input slider, terminates input to a touch-sensitive input area, etc.), a new user input prompt "How many hours do you sleep in a normal 24 hour period?" may be displayed (e.g., as shown in FIG. 6B). As such, user input may be rapidly captured for various user input prompts (e.g., as subsequent user input prompts may automatically be displayed in response to user input release from touch-sensitive input areas).

Additionally, FIGS. 6A and 6B show an example where the input slider reverts from a second state (e.g., the state indicative of user input to the touch-sensitive input area, as shown in FIG. 6A) to the first state (e.g., the state indicative of no user input to the touch-sensitive input area, as shown in FIG. 6B) upon detection that the user input to the sensitive input area has been terminated. As described herein, the change of input bar states may include a change in line color of the input bar, a change in line thickness or line dash style of the input bar, etc.

Figure 7C:
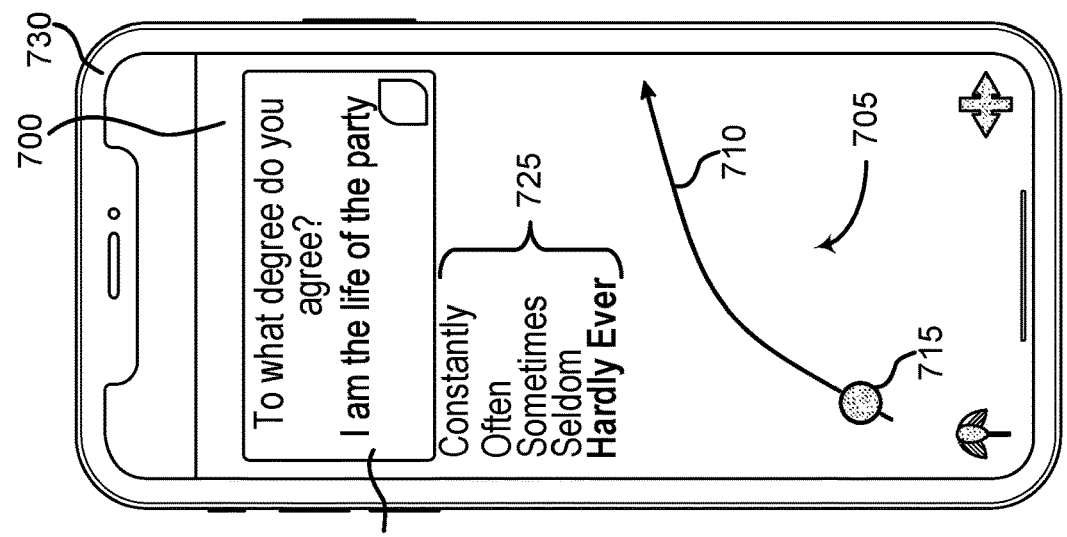
FIGS. 7A-7C and 8 show examples of a system for rapidly capturing user input according to aspects of the present disclosure.
Figure 7B:
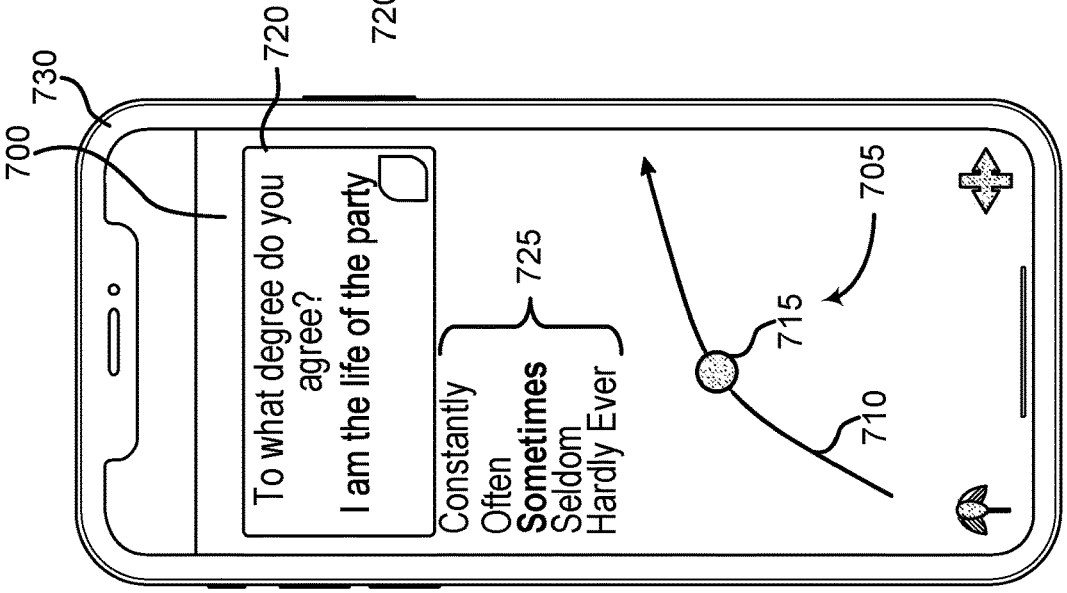
Figure 7A:
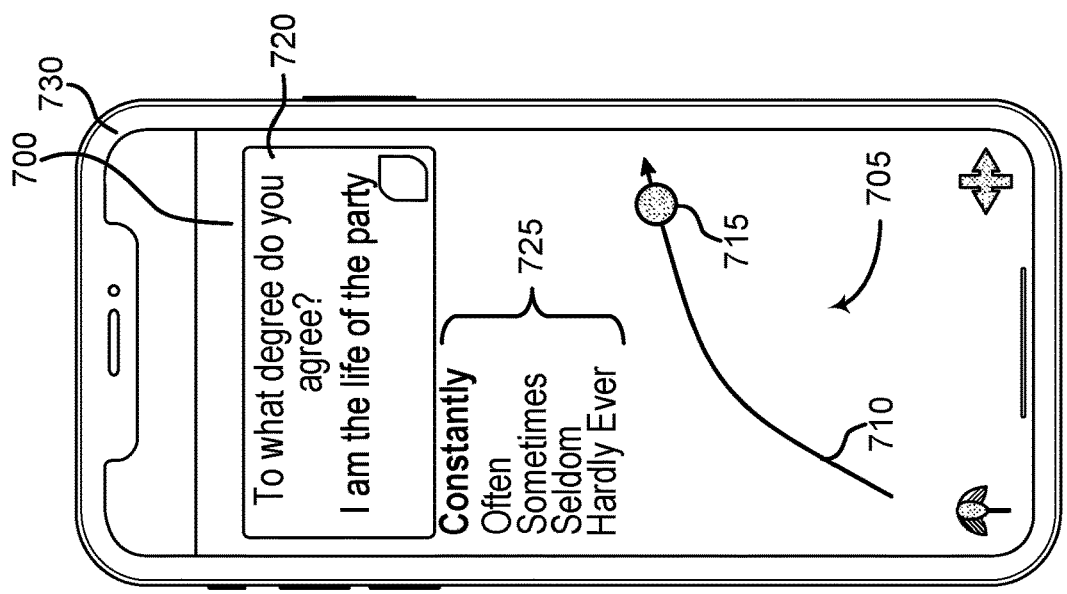

FIGS. 7A-7C show an example of a system for rapidly capturing user input according to aspects of the present disclosure. The example shown includes visual display screen 700 and housing 730.

Visual display screen 700 is an example of, or includes aspects of, the corresponding element described with reference to FIGS. 1, 2, 4, 5, and 8. In one embodiment, visual display screen 700 includes touch-sensitive input area 705, input prompt 720, and input indicator 725. Touch-sensitive input area 705 is an example of, or includes aspects of, the corresponding element described with reference to FIGS. 1, 2, 4, 5, and 8. In one embodiment, touch-sensitive input area 705 includes input bar 710 and input position 715. Input bar 710 is an example of, or includes aspects of, the corresponding element described with reference to FIGS. 2, 4, 5, and 8. Input position 715 is an example of, or includes aspects of, the corresponding element described with reference to FIGS. 2, 4, 5, and 8.

Input prompt 720 is an example of, or includes aspects of, the corresponding element described with reference to FIGS. 2, 4, 5, and 8. Input indicator 725 is an example of, or includes aspects of, the corresponding element described with reference to FIGS. 4, 5, and 8.

Housing 730 is an example of, or includes aspects of, the corresponding element described with reference to FIGS. 1, 2, 4, 5, and 8.

FIGS. 7A-7C illustrate another example of input indicators 725 providing visual indication of user input (e.g., of user selected input position 715 along the length of the input bar 710 arc). FIGS. 7A-7C show an example where a user input prompt 720 prompts user input to the phrase "To what degree do you agree? I am the life of the party," (e.g., prompting user input regarding whether the user agrees they are the life of the party). As the input position 715 is adjusted along the length of the input bar 710, the input indicator 725 indicates corresponding user input. For instance, in FIG. 7A, the input position 715 is at the top of the length of the input bar 710, and the input indicator 725 shows a bolded "Constantly." In FIG. 7B, as the slider is moved down (e.g., and the input position 715 is adjusted down the length of the input bar 710), the input indicator 725 indicates corresponding user input by moving the bolded font down the list of options displayed in the input indicator 725. In FIG. 7C, the input position 715 is at the bottom of the length of the input bar 710, and the input indicator 725 shows a bolded "Hardly Ever." In this way, the system is able to quickly inquire as to the user's response, and the user is able to quickly and efficiently response with their response, where their response includes a degree of response, e.g., "constantly" to "never", over a seemingly continuous range of response options between two extremes.

Figure 8:
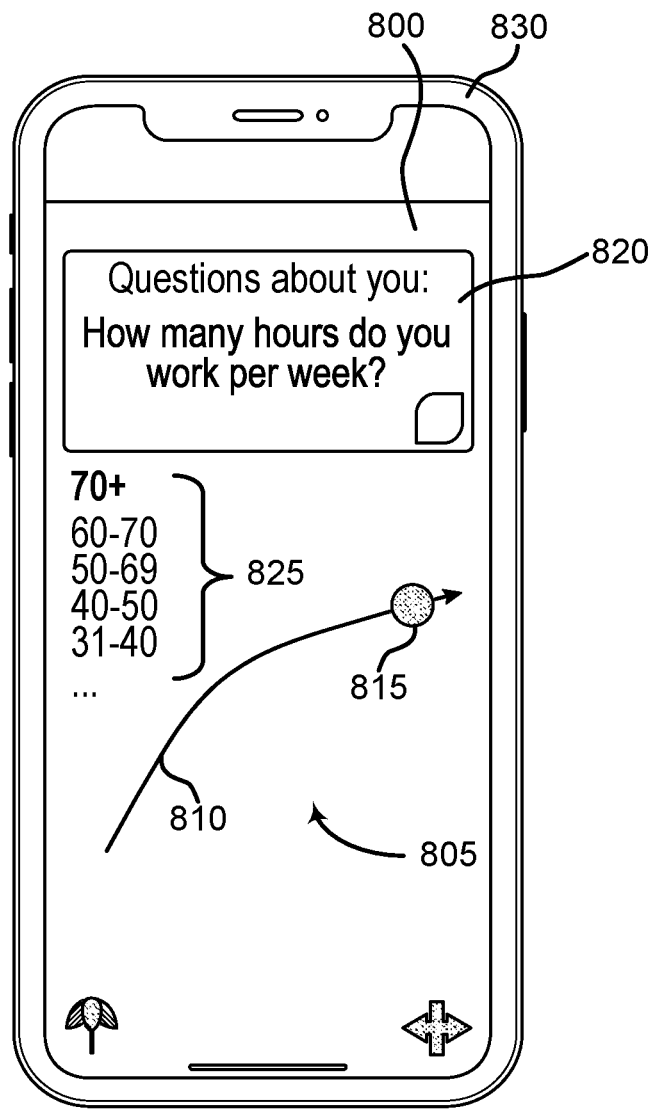

FIG. 8 shows an example of a system for rapidly capturing user input according to aspects of the present disclosure. The example shown includes visual display screen 800 and housing 830.

Visual display screen 800 is an example of, or includes aspects of, the corresponding element described with reference to FIGS. 1, 2, 4, 5, and 7. In one embodiment, visual display screen 800 includes touch-sensitive input area 805, input prompt 820, and input indicator 825. Touch-sensitive input area 805 is an example of, or includes aspects of, the corresponding element described with reference to FIGS. 1, 2, 4, 5, and 7. In one embodiment, touch-sensitive input area 805 includes input bar 810 and input position 815. Input bar 810 is an example of, or includes aspects of, the corresponding element described with reference to FIGS. 2, 4, 5, and 7. Input position 815 is an example of, or includes aspects of, the corresponding element described with reference to FIGS. 2, 4, 5, and 7.

Input prompt 820 is an example of, or includes aspects of, the corresponding element described with reference to FIGS. 2, 4, 5, and 7. Input indicator 825 is an example of, or includes aspects of, the corresponding element described with reference to FIGS. 4, 5, and 7.

Housing 830 is an example of, or includes aspects of, the corresponding element described with reference to FIGS. 1, 2, 4, 5, and 7.

FIG. 8 shows another example of an input indicator 825 providing visual indication of user input (e.g., of user selected input position 815 along the length of the input bar 810 arc). FIG. 8 shows an example where a user input prompt 820 prompts user input to the phrase "How many hours do you work per week," (e.g., prompting user input regarding how many hours the user works per week). As the input position 815 is adjusted along the length of the input bar 810, the input indicator 825 indicates corresponding user input. For instance, in FIG. 8, the input position 815 is at the top of the length of the input bar 810, and the input indicator 825 shows a bolded "70+" (e.g., indicating user input of 70 hours or more per week). If the slider is moved down (e.g., and the input position 815 is adjusted down the length of the input bar 810), the input indicator 825 may bold other corresponding user input by moving the bolded font down the list of options displayed in the input indicator 825.

Figure 9:
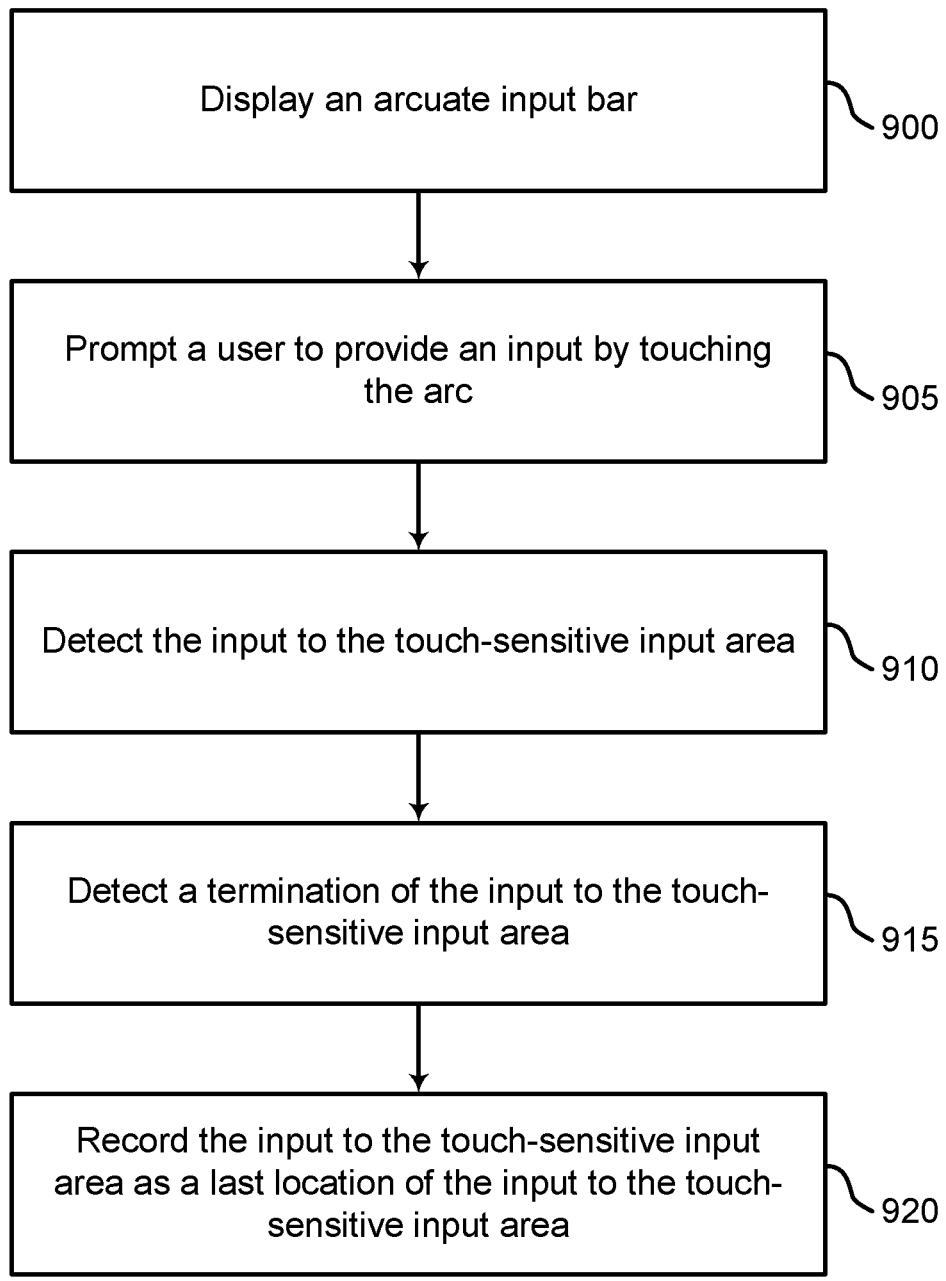
FIGS. 9 through 17 show examples of a process for rapidly capturing user input according to aspects of the present disclosure.

FIG. 9 shows an example of a process for rapidly capturing user input according to aspects of the present disclosure. In some examples, these operations are performed by a system including a processor executing a set of codes to control functional elements of an apparatus. Additionally or alternatively, certain processes are performed using special-purpose hardware. Generally, these operations are performed according to the methods and processes described in accordance with aspects of the present disclosure. In some cases, the operations described herein are composed of various substeps, or are performed in conjunction with other operations.

At operation 900, the system displays an arcuate input bar, the arcuate input bar being an arc with a radius originating from a segment of an edge defining at least a portion of a periphery of a surface of a housing. In some cases, the operations of this step refer to, or may be performed by, a visual display screen as described with reference to FIGS. 1, 2, 4, 5, 7, and 8.

At operation 905, the system prompts a user to provide an input by touching the arc with a finger at one or more points along a length of the arc, thereby providing input to a touch-sensitive input area of a visual display screen. In some cases, the operations of this step refer to, or may be performed by, a visual display screen as described with reference to FIGS. 1, 2, 4, 5, 7, and 8.

At operation 910, the system detects the input to the touch-sensitive input area, including detecting a position along the arc of the input to the touch-sensitive input area. In some cases, the operations of this step refer to, or may be performed by, a touch-sensitive input area as described with reference to FIGS. 1, 2, 4, 5, 7, and 8.

At operation 915, the system detects a termination of the input to the touch-sensitive input area. In some cases, the operations of this step refer to, or may be performed by, a touch-sensitive input area as described with reference to FIGS. 1, 2, 4, 5, 7, and 8.

At operation 920, the system records the input to the touch-sensitive input area as a last location of the input to the touch-sensitive input area preceding the detecting of the termination of the input to the touch-sensitive input area. In some cases, the operations of this step refer to, or may be performed by, a memory as described with reference to FIG. 1.

Figure 10:
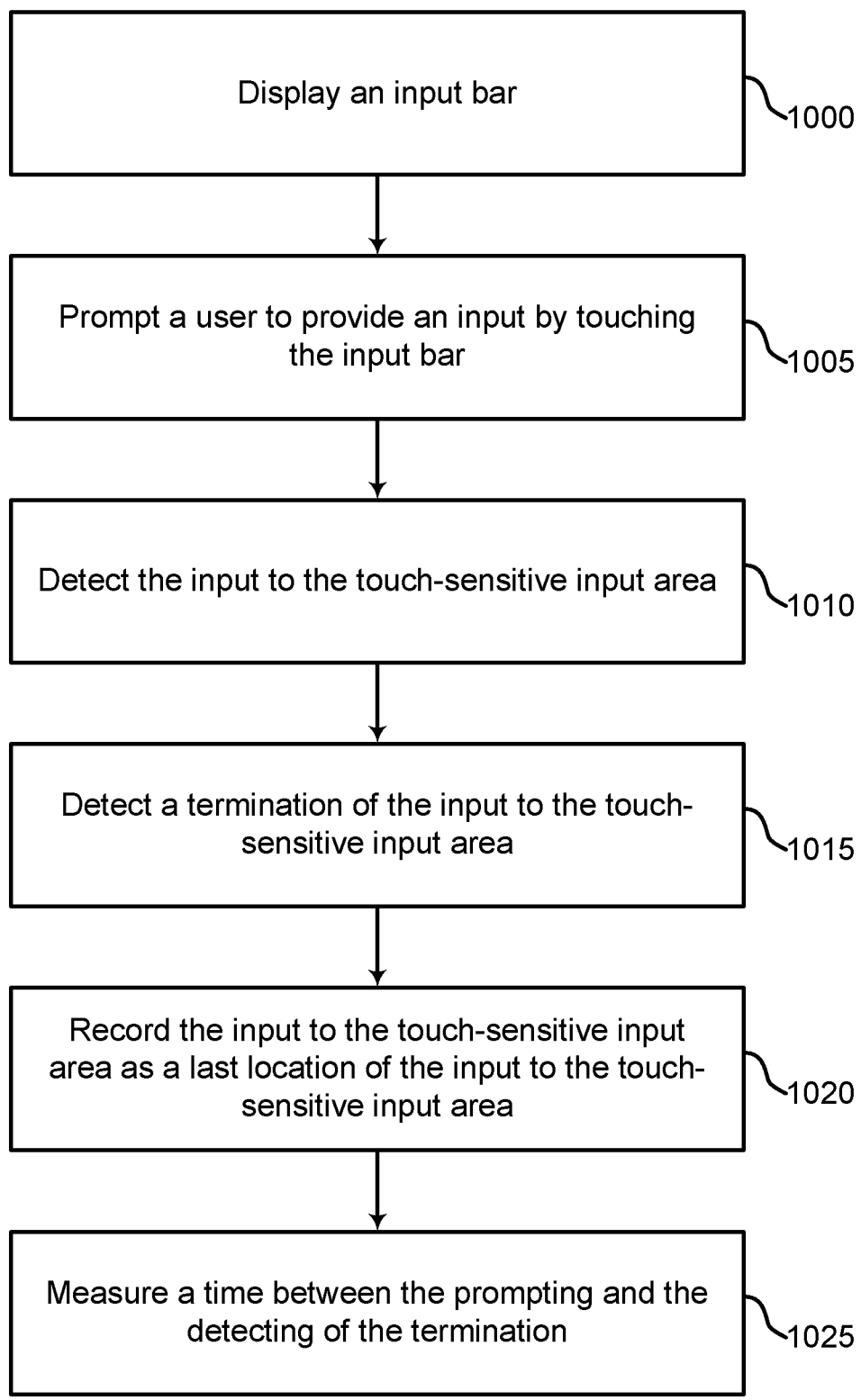

FIG. 10 shows an example of a process for rapidly capturing user input according to aspects of the present disclosure. In some examples, these operations are performed by a system including a processor executing a set of codes to control functional elements of an apparatus. Additionally or alternatively, certain processes are performed using special-purpose hardware. Generally, these operations are performed according to the methods and processes described in accordance with aspects of the present disclosure. In some cases, the operations described herein are composed of various substeps, or are performed in conjunction with other operations.

At operation 1000, the system displays an input bar. In some cases, the operations of this step refer to, or may be performed by, a visual display screen as described with reference to FIGS. 1, 2, 4, 5, 7, and 8.

At operation 1005, the system prompts a user to provide an input by touching the input bar with a finger at one or more points along a length of the input bar, thereby providing input to a touch-sensitive input area of a visual display screen. In some cases, the operations of this step refer to, or may be performed by, a visual display screen as described with reference to FIGS. 1, 2, 4, 5, 7, and 8.

At operation 1010, the system detects the input to the touch-sensitive input area, including detecting a position along the input bar of the input to the touch-sensitive input area. In some cases, the operations of this step refer to, or may be performed by, a touch-sensitive input area as described with reference to FIGS. 1, 2, 4, 5, 7, and 8.

At operation 1015, the system detects a termination of the input to the touch-sensitive input area. In some cases, the operations of this step refer to, or may be performed by, a touch-sensitive input area as described with reference to FIGS. 1, 2, 4, 5, 7, and 8.

At operation 1020, the system records the input to the touch-sensitive input area as a last location of the input to the touch-sensitive input area preceding the detecting of the termination of the input to the touch-sensitive input area. In some cases, the operations of this step refer to, or may be performed by, a memory as described with reference to FIG. 1.

At operation 1025, the system measures a time between the prompting and the detecting of the termination, where recording to the memory the input to the touch-sensitive input area further includes recording the time. In some cases, the operations of this step refer to, or may be performed by, a processor as described with reference to FIG. 1.

Figure 11:
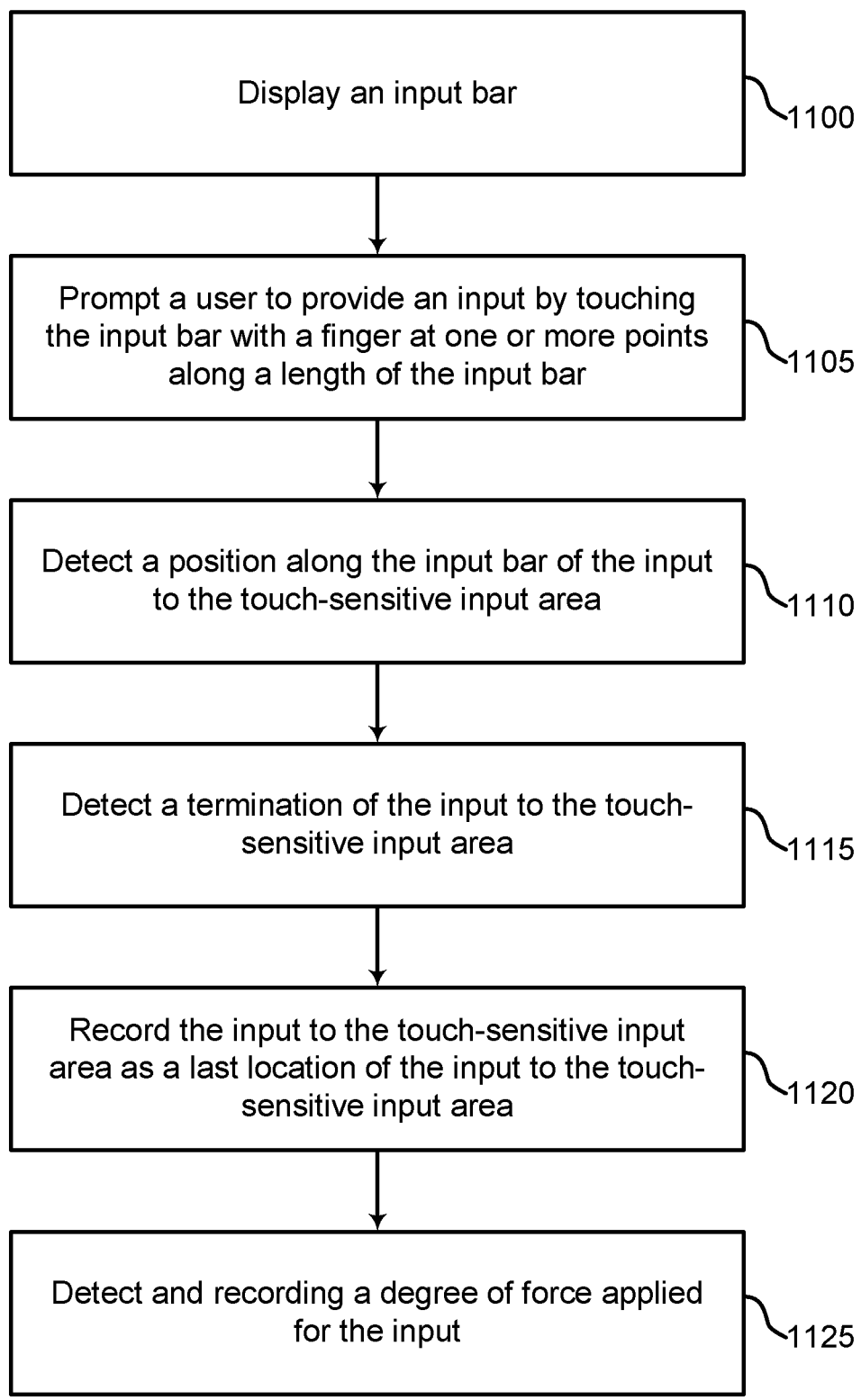

FIG. 11 shows an example of a process for rapidly capturing user input according to aspects of the present disclosure. In some examples, these operations are performed by a system including a processor executing a set of codes to control functional elements of an apparatus. Additionally or alternatively, certain processes are performed using special-purpose hardware. Generally, these operations are performed according to the methods and processes described in accordance with aspects of the present disclosure. In some cases, the operations described herein are composed of various substeps, or are performed in conjunction with other operations.

At operation 1100, the system displays an input bar. In some cases, the operations of this step refer to, or may be performed by, a visual display screen as described with reference to FIGS. 1, 2, 4, 5, 7, and 8.

At operation 1105, the system prompts a user to provide an input by touching the input bar with a finger at one or more points along a length of the input bar, thereby providing input to a touch-sensitive input area of a visual display screen. In some cases, the operations of this step refer to, or may be performed by, a visual display screen as described with reference to FIGS. 1, 2, 4, 5, 7, and 8.

At operation 1110, the system detects the input to the touch-sensitive input area, including detecting a position along the input bar of the input to the touch-sensitive input area. In some cases, the operations of this step refer to, or may be performed by, a touch-sensitive input area as described with reference to FIGS. 1, 2, 4, 5, 7, and 8.

At operation 1115, the system detects a termination of the input to the touch-sensitive input area. In some cases, the operations of this step refer to, or may be performed by, a touch-sensitive input area as described with reference to FIGS. 1, 2, 4, 5, 7, and 8.

At operation 1120, the system records, to memory, the input to the touch-sensitive input area as a last location of the input to the touch-sensitive input area preceding the detecting of the termination of the input to the touch-sensitive input area. In some cases, the operations of this step refer to, or may be performed by, a memory as described with reference to FIG. 1.

At operation 1125, the system detects the input to the touch-sensitive input area, including detecting a degree of force applied for the input, where recording the input to the touch-sensitive input area further includes recording the degree of force. In some cases, the operations of this step refer to, or may be performed by, a processor as described with reference to FIG. 1.

Figure 12:
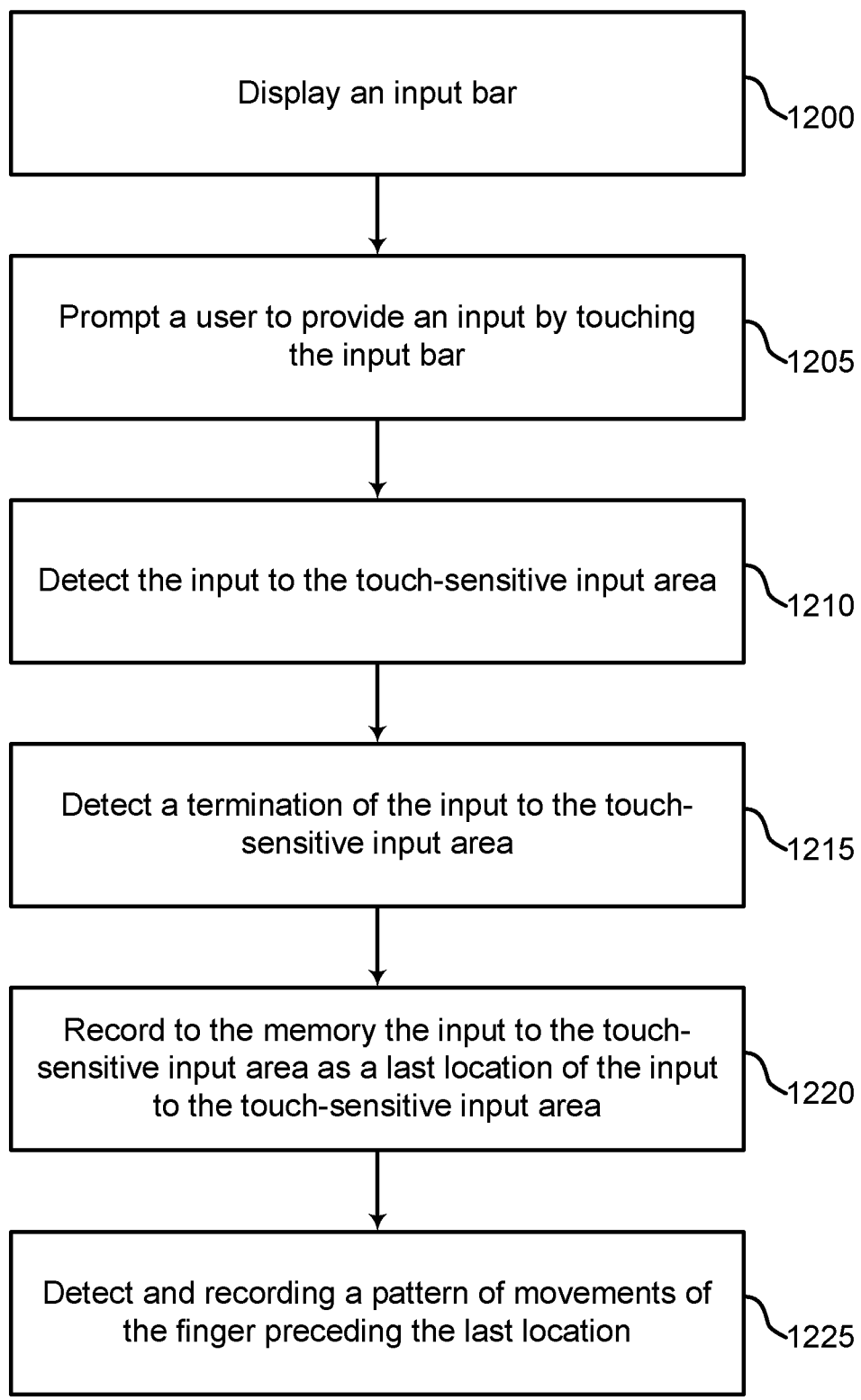

FIG. 12 shows an example of a process for rapidly capturing user input according to aspects of the present disclosure. In some examples, these operations are performed by a system including a processor executing a set of codes to control functional elements of an apparatus. Additionally or alternatively, certain processes are performed using special-purpose hardware. Generally, these operations are performed according to the methods and processes described in accordance with aspects of the present disclosure. In some cases, the operations described herein are composed of various substeps, or are performed in conjunction with other operations.

At operation 1200, the system displays an input bar. In some cases, the operations of this step refer to, or may be performed by, a visual display screen as described with reference to FIGS. 1, 2, 4, 5, 7, and 8.

At operation 1205, the system prompts a user to provide an input by touching the input bar with a finger at one or more points along a length of the input bar, thereby providing an input to a touch-sensitive input area of a visual display screen. In some cases, the operations of this step refer to, or may be performed by, a visual display screen as described with reference to FIGS. 1, 2, 4, 5, 7, and 8.

At operation 1210, the system detects the input to the touch-sensitive input area, including detecting a position along the input bar of the input to the touch-sensitive input area. In some cases, the operations of this step refer to, or may be performed by, a touch-sensitive input area as described with reference to FIGS. 1, 2, 4, 5, 7, and 8.

At operation 1215, the system detects a termination of the input to the touch-sensitive input area. In some cases, the operations of this step refer to, or may be performed by, a touch-sensitive input area as described with reference to FIGS. 1, 2, 4, 5, 7, and 8.

At operation 1220, the system records to the memory the input to the touch-sensitive input area as a last location of the input to the touch-sensitive input area preceding the detecting of the termination of the input to the touch-sensitive input area. In some cases, the operations of this step refer to, or may be performed by, a memory as described with reference to FIG. 1.

At operation 1225, the system detects the input to the touch-sensitive input area, including detecting a pattern of movements of the finger preceding the last location, where recording the input to the touch-sensitive input area further includes recording the pattern of movements. In some cases, the operations of this step refer to, or may be performed by, a processor as described with reference to FIG. 1.

Figure 13:
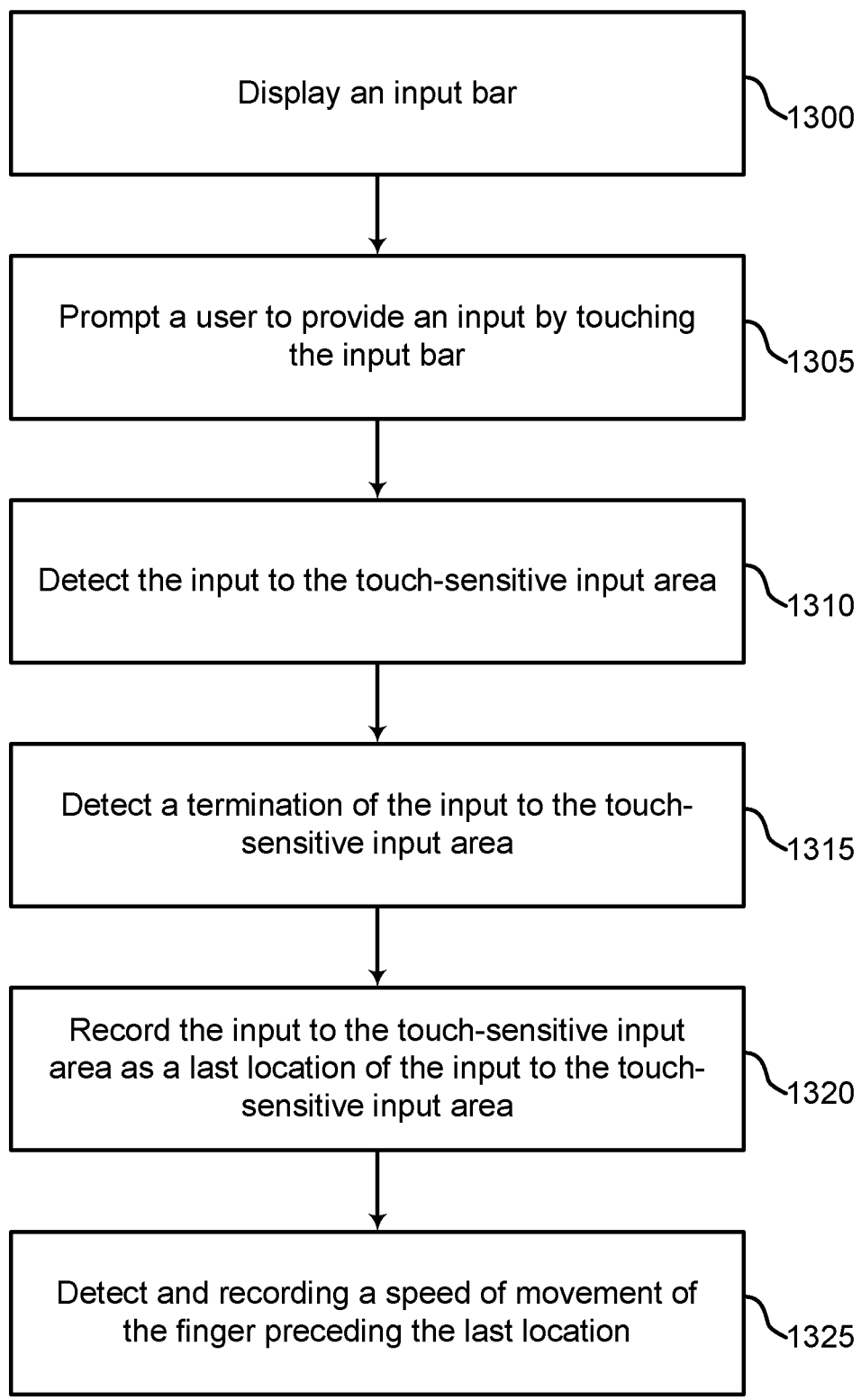

FIG. 13 shows an example of a process for rapidly capturing user input according to aspects of the present disclosure. In some examples, these operations are performed by a system including a processor executing a set of codes to control functional elements of an apparatus. Additionally or alternatively, certain processes are performed using special-purpose hardware. Generally, these operations are performed according to the methods and processes described in accordance with aspects of the present disclosure. In some cases, the operations described herein are composed of various substeps, or are performed in conjunction with other operations.

At operation 1300, the system displays an input bar. In some cases, the operations of this step refer to, or may be performed by, a visual display screen as described with reference to FIGS. 1, 2, 4, 5, 7, and 8.

At operation 1305, the system prompts a user to provide an input by touching the input bar with a finger at one or more points along a length of the input bar, thereby providing an input to a touch-sensitive input area of a visual display screen. In some cases, the operations of this step refer to, or may be performed by, a visual display screen as described with reference to FIGS. 1, 2, 4, 5, 7, and 8.

At operation 1310, the system detects the input to the touch-sensitive input area, including detecting a position along the input bar of the input to the touch-sensitive input area. In some cases, the operations of this step refer to, or may be performed by, a touch-sensitive input area as described with reference to FIGS. 1, 2, 4, 5, 7, and 8.

At operation 1315, the system detects a termination of the input to the touch-sensitive input area. In some cases, the operations of this step refer to, or may be performed by, a touch-sensitive input area as described with reference to FIGS. 1, 2, 4, 5, 7, and 8.

At operation 1320, the system records the input to the touch-sensitive input area as a last location of the input to the touch-sensitive input area preceding the detecting of the termination of the input to the touch-sensitive input area. In some cases, the operations of this step refer to, or may be performed by, a memory as described with reference to FIG. 1.

At operation 1325, the system detects the input to the touch-sensitive input area, including detecting a speed of movement of the finger preceding the last location, where recording the input to the touch-sensitive input area further includes recording the speed of movement of the finger preceding the last location. In some cases, the operations of this step refer to, or may be performed by, a processor as described with reference to FIG. 1.

Figure 14:
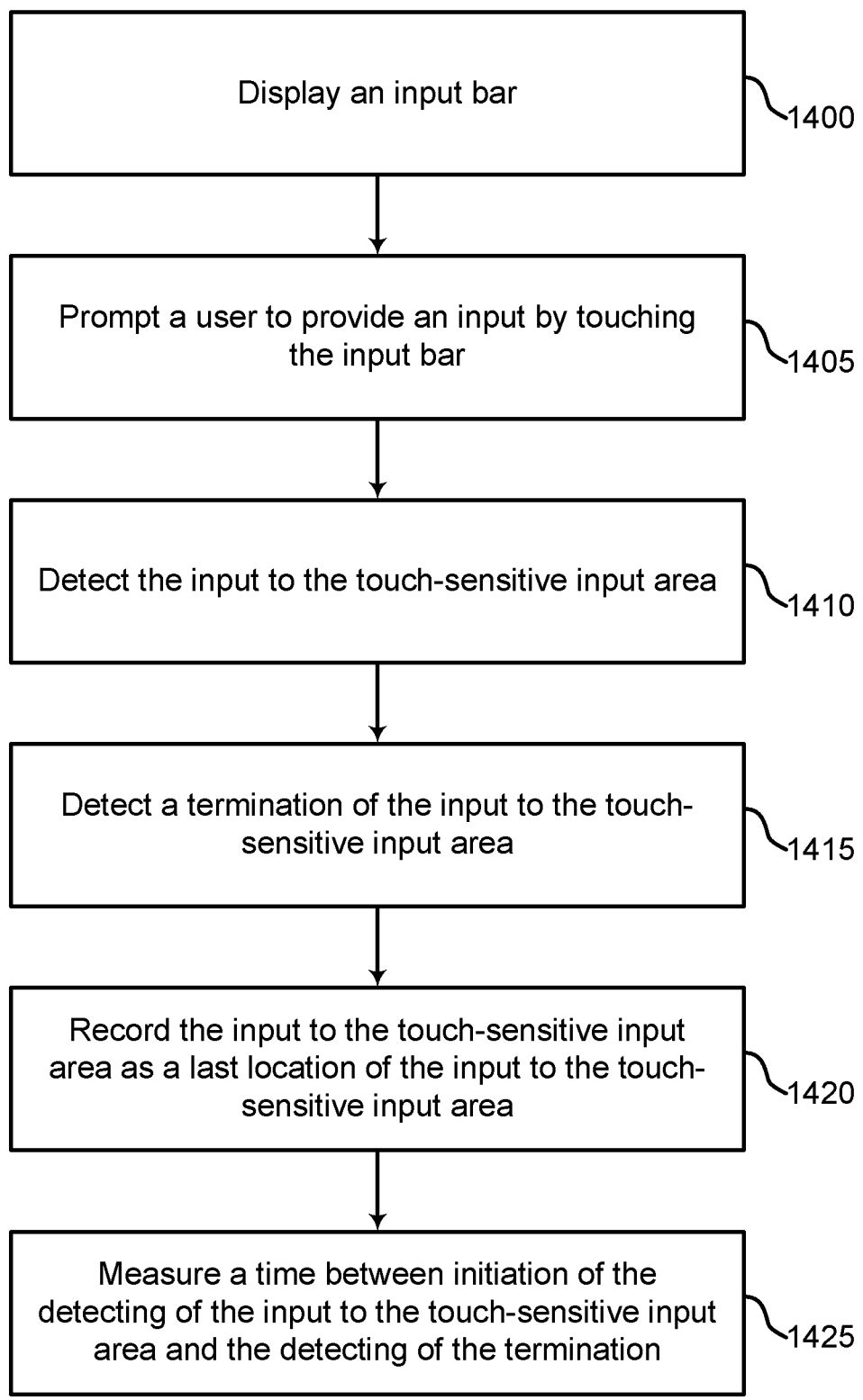

FIG. 14 shows an example of a process for rapidly capturing user input according to aspects of the present disclosure. In some examples, these operations are performed by a system including a processor executing a set of codes to control functional elements of an apparatus. Additionally or alternatively, certain processes are performed using special-purpose hardware. Generally, these operations are performed according to the methods and processes described in accordance with aspects of the present disclosure. In some cases, the operations described herein are composed of various substeps, or are performed in conjunction with other operations.

At operation 1400, the system displays an input bar. In some cases, the operations of this step refer to, or may be performed by, a visual display screen as described with reference to FIGS. 1, 2, 4, 5, 7, and 8.

At operation 1405, the system prompts a user to provide an input by touching the input bar with a finger at one or more points along a length of the input bar, thereby providing an input to a touch-sensitive input area of a visual display screen. In some cases, the operations of this step refer to, or may be performed by, a visual display screen as described with reference to FIGS. 1, 2, 4, 5, 7, and 8.

At operation 1410, the system detects the input to the touch-sensitive input area, including detecting a position along the input bar of the input to the touch-sensitive input area. In some cases, the operations of this step refer to, or may be performed by, a touch-sensitive input area as described with reference to FIGS. 1, 2, 4, 5, 7, and 8.

At operation 1415, the system detects a termination of the input to the touch-sensitive input area. In some cases, the operations of this step refer to, or may be performed by, a touch-sensitive input area as described with reference to FIGS. 1, 2, 4, 5, 7, and 8.

At operation 1420, the system records the input to the touch-sensitive input area as a last location of the input to the touch-sensitive input area preceding the detecting of the termination of the input to the touch-sensitive input area. In some cases, the operations of this step refer to, or may be performed by, a memory as described with reference to FIG. 1.

At operation 1425, the system measures a time between initiation of the detecting of the input to the touch-sensitive input area and the detecting of the termination, where recording the input to the touch-sensitive input area further includes recording the time. In some cases, the operations of this step refer to, or may be performed by, a processor as described with reference to FIG. 1.

Figure 15:
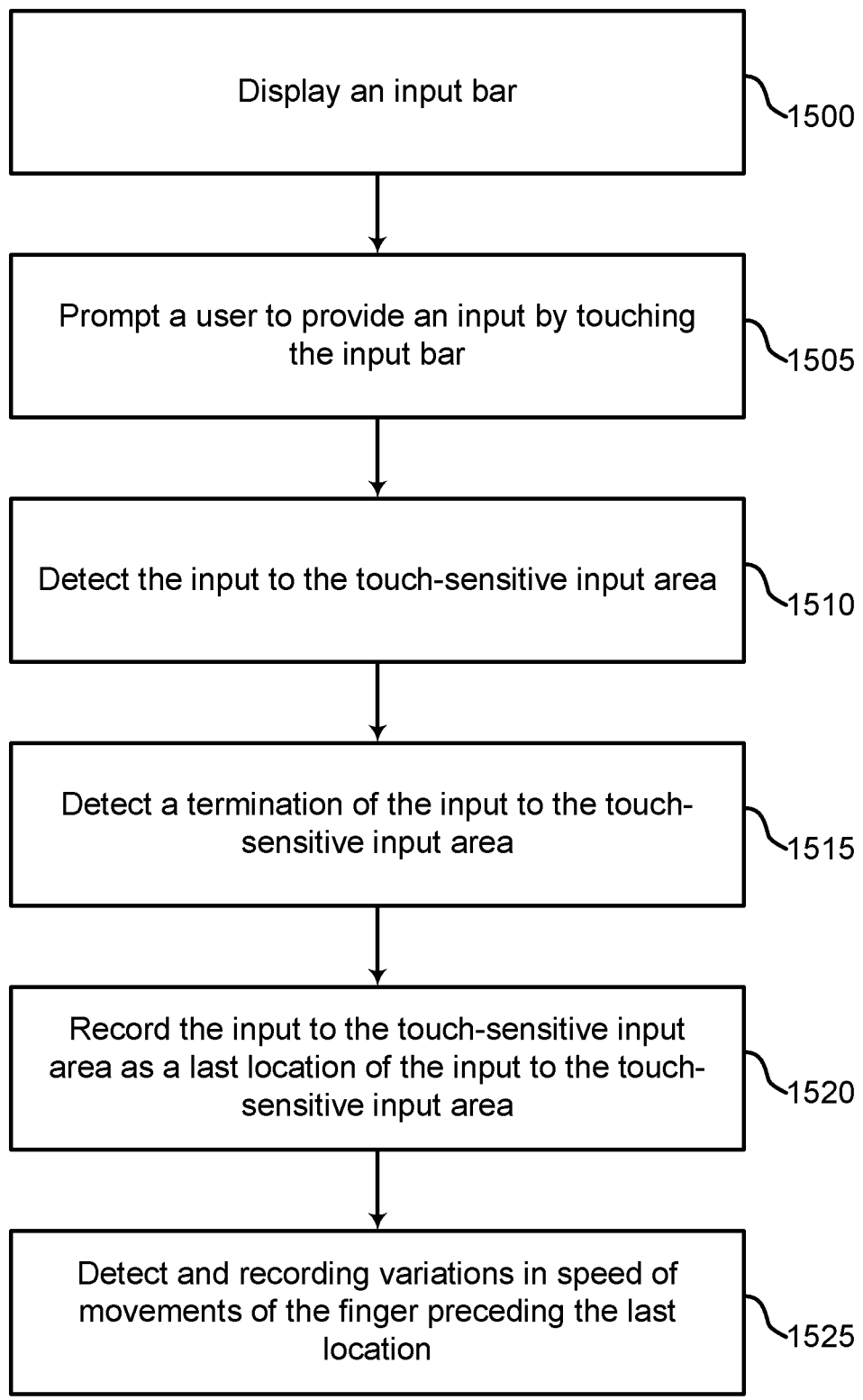

FIG. 15 shows an example of a process for rapidly capturing user input according to aspects of the present disclosure. In some examples, these operations are performed by a system including a processor executing a set of codes to control functional elements of an apparatus. Additionally or alternatively, certain processes are performed using special-purpose hardware. Generally, these operations are performed according to the methods and processes described in accordance with aspects of the present disclosure. In some cases, the operations described herein are composed of various substeps, or are performed in conjunction with other operations.

At operation 1500, the system displays an input bar. In some cases, the operations of this step refer to, or may be performed by, a visual display screen as described with reference to FIGS. 1, 2, 4, 5, 7, and 8.

At operation 1505, the system prompts a user to provide an input by touching the input bar with a finger at one or more points along a length of the input bar, thereby providing an input to a touch-sensitive input area of a visual display screen. In some cases, the operations of this step refer to, or may be performed by, a visual display screen as described with reference to FIGS. 1, 2, 4, 5, 7, and 8.

At operation 1510, the system detects the input to the touch-sensitive input area, including detecting a position along the input bar of the input to the touch-sensitive input area. In some cases, the operations of this step refer to, or may be performed by, a touch-sensitive input area as described with reference to FIGS. 1, 2, 4, 5, 7, and 8.

At operation 1515, the system detects a termination of the input to the touch-sensitive input area. In some cases, the operations of this step refer to, or may be performed by, a touch-sensitive input area as described with reference to FIGS. 1, 2, 4, 5, 7, and 8.

At operation 1520, the system records the input to the touch-sensitive input area as a last location of the input to the touch-sensitive input area preceding the detecting of the termination of the input to the touch-sensitive input area. In some cases, the operations of this step refer to, or may be performed by, a memory as described with reference to FIG. 1.

At operation 1525, the system detects the input to the touch-sensitive input area, including detecting variations in speed of movements of the finger preceding the last location, where the recording the input to the touch-sensitive input area further includes recording the variations in speed of movements. In some cases, the operations of this step refer to, or may be performed by, a processor as described with reference to FIG. 1.

Figure 16:
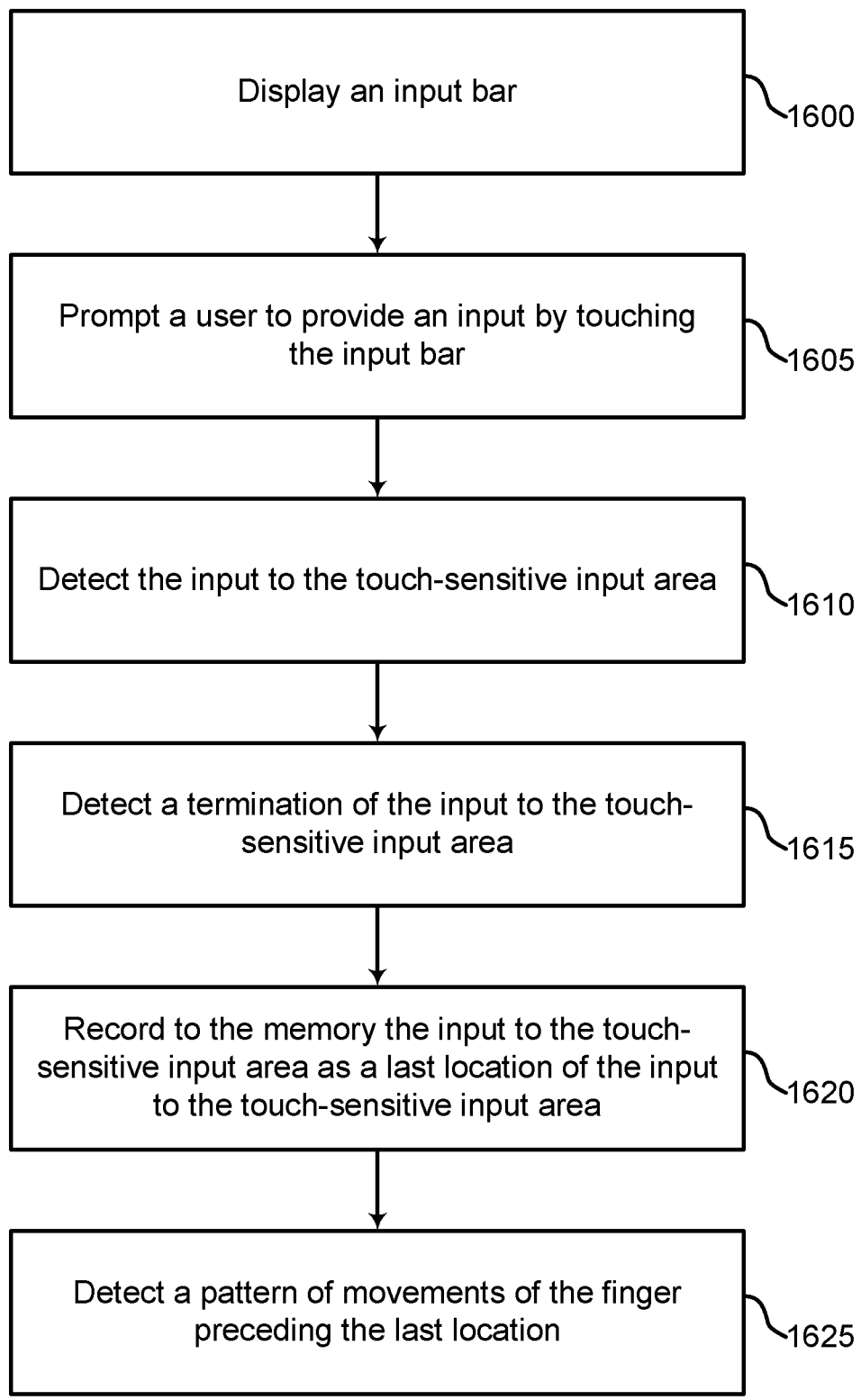

FIG. 16 shows an example of a process for rapidly capturing user input according to aspects of the present disclosure. In some examples, these operations are performed by a system including a processor executing a set of codes to control functional elements of an apparatus. Additionally or alternatively, certain processes are performed using special-purpose hardware. Generally, these operations are performed according to the methods and processes described in accordance with aspects of the present disclosure. In some cases, the operations described herein are composed of various substeps, or are performed in conjunction with other operations.

At operation 1600, the system displays an input bar. In some cases, the operations of this step refer to, or may be performed by, a visual display screen as described with reference to FIGS. 1, 2, 4, 5, 7, and 8.

At operation 1605, the system prompts a user to provide an input by touching the input bar with a finger at one or more points along a length of the input bar, thereby providing an input to a touch-sensitive input area of a visual display screen. In some cases, the operations of this step refer to, or may be performed by, a visual display screen as described with reference to FIGS. 1, 2, 4, 5, 7, and 8.

At operation 1610, the system detects the input to the touch-sensitive input area, including detecting a position along the input bar of the input to the touch-sensitive input area. In some cases, the operations of this step refer to, or may be performed by, a touch-sensitive input area as described with reference to FIGS. 1, 2, 4, 5, 7, and 8.

At operation 1615, the system detects a termination of the input to the touch-sensitive input area. In some cases, the operations of this step refer to, or may be performed by, a touch-sensitive input area as described with reference to FIGS. 1, 2, 4, 5, 7, and 8.

At operation 1620, the system records to the memory the input to the touch-sensitive input area as a last location of the input to the touch-sensitive input area preceding the detecting of the termination of the input to the touch-sensitive input area. In some cases, the operations of this step refer to, or may be performed by, a memory as described with reference to FIG. 1.

At operation 1625, the system detects the input to the touch-sensitive input area, including detecting a pattern of movements of the finger preceding the last location, where recording the input to the touch-sensitive input area further includes recording the pattern of movements. In some cases, the operations of this step refer to, or may be performed by, a processor as described with reference to FIG. 1.

Figure 17:
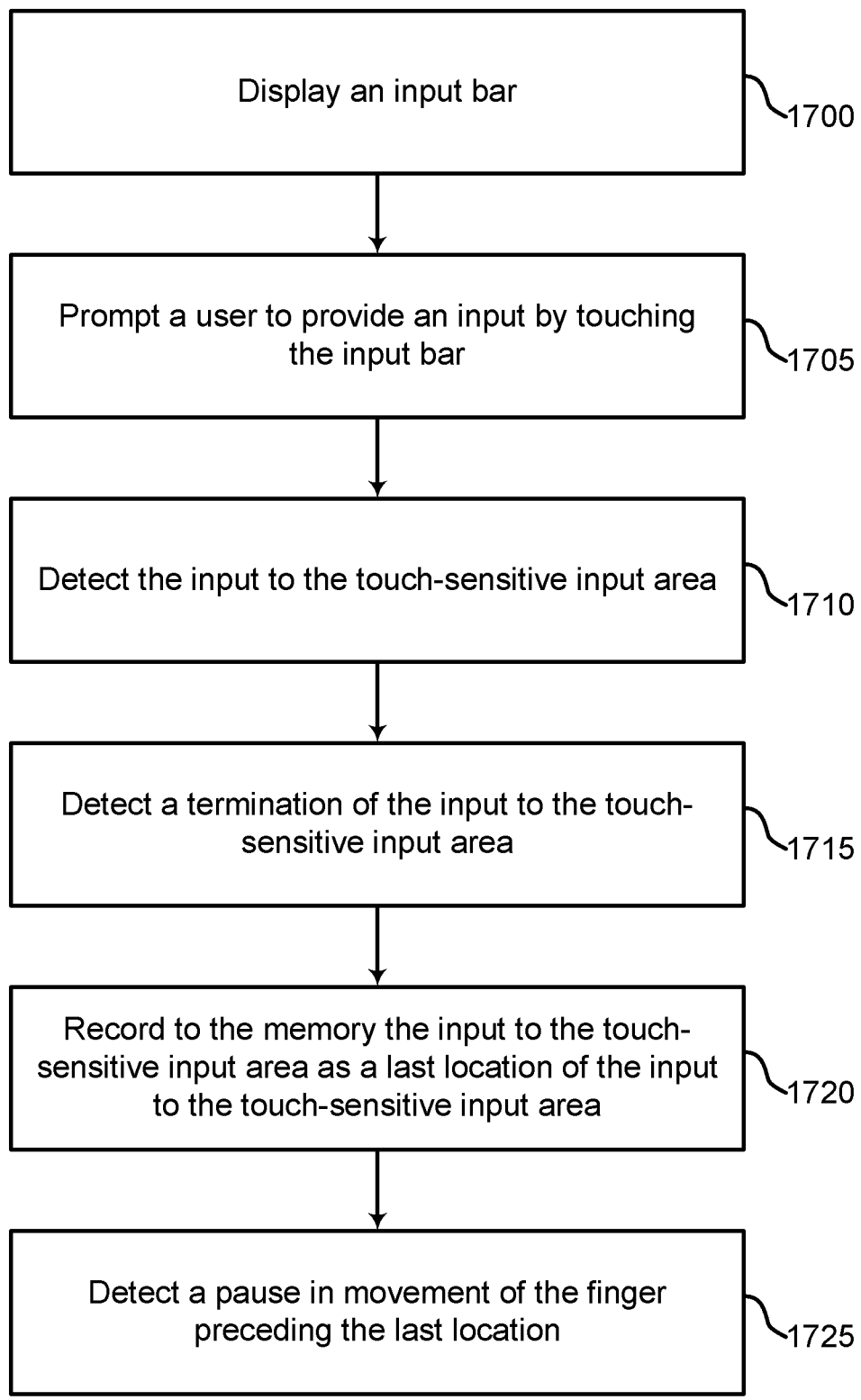

FIG. 17 shows an example of a process for rapidly capturing user input according to aspects of the present disclosure. In some examples, these operations are performed by a system including a processor executing a set of codes to control functional elements of an apparatus. Additionally or alternatively, certain processes are performed using special-purpose hardware. Generally, these operations are performed according to the methods and processes described in accordance with aspects of the present disclosure. In some cases, the operations described herein are composed of various substeps, or are performed in conjunction with other operations.

At operation 1700, the system displays an input bar. In some cases, the operations of this step refer to, or may be performed by, a visual display screen as described with reference to FIGS. 1, 2, 4, 5, 7, and 8.

At operation 1705, the system prompts a user to provide an input by touching the input bar with a finger at one or more points along a length of the input bar, thereby providing an input to a touch-sensitive input area of a visual display screen. In some cases, the operations of this step refer to, or may be performed by, a visual display screen as described with reference to FIGS. 1, 2, 4, 5, 7, and 8.

At operation 1710, the system detects the input to the touch-sensitive input area, including detecting a position along the input bar of the input to the touch-sensitive input area. In some cases, the operations of this step refer to, or may be performed by, a touch-sensitive input area as described with reference to FIGS. 1, 2, 4, 5, 7, and 8.

At operation 1715, the system detects a termination of the input to the touch-sensitive input area. In some cases, the operations of this step refer to, or may be performed by, a touch-sensitive input area as described with reference to FIGS. 1, 2, 4, 5, 7, and 8.

At operation 1720, the system records to the memory the input to the touch-sensitive input area as a last location of the input to the touch-sensitive input area preceding the detecting of the termination of the input to the touch-sensitive input area. In some cases, the operations of this step refer to, or may be performed by, a memory as described with reference to FIG. 1.

At operation 1725, the system detects the input to the touch-sensitive input area, including detecting a pause in movement of the finger preceding the last location, where recording the input to the touch-sensitive input area further includes recording the pause in movement. In some cases, the operations of this step refer to, or may be performed by, a processor as described with reference to FIG. 1.

Accordingly, the present disclosure includes the following embodiments.

A system for rapidly capturing user input, the system comprising: a visual display screen having a surface area, a housing having an edge, and a surface, the edge defining at least a portion of a periphery of the surface, and the surface comprised at least in part by the visual display screen, a touch-sensitive input area, the touch-sensitive input area being across at least a portion of the surface area, a memory, and a processor within the housing and operatively coupled to the visual display screen, the memory and the touch-sensitive input area, wherein the processor comprises software for displaying an arcuate input bar, the arcuate input bar being an arc with a radius originating from a segment of the edge; prompting a user to provide an input by touching the arc with a finger at one or more points along a length of the arc, thereby providing input to the touch-sensitive input area; detecting the input to the touch-sensitive input area, including detecting a position along the arc of the input to the touch-sensitive input area; detecting a termination of the input to the touch-sensitive input area; and recording, to the memory, the input to the touch-sensitive input area as a last location of the input to the touch-sensitive input area preceding the detecting of the termination of the input to the touch-sensitive input area.

In some examples, the software may include software for displaying a cursor feature along the arc at the position along the arc of the input to the touch-sensitive input area.

In some examples, the software may include software for displaying at least one target along the arc.

In some examples, the detecting of the input to the touch-sensitive input area further comprises detecting the position along the arc of the input to the touch-sensitive input area when the position corresponds to at least one target along the arc.

In some examples, the software may include software for displaying a response indicia separate from the arcuate input bar and varying the response indicia as a function of the position along the arc of the input to the touch-sensitive input area.

In some examples, the software may include software for displaying a plurality of targets along the arc.

In some examples, the software may include software for measuring a time between the prompting and the detecting of the termination, and where recording the input to the touch-sensitive input area further comprises recording the time.

In some examples, the software may include software for detecting the input to the touch-sensitive input area, including detecting a degree of force applied for the input, and where recording the input to the touch-sensitive input area further comprises recording the degree of force.

In some examples, the software may include software for detecting the input to the touch-sensitive input area, including detecting a pattern of movements of the finger preceding the last location, and where recording the input to the touch-sensitive input area further comprises recording the pattern of movements.

In some examples, the software may include software for detecting the input to the touch-sensitive input area, including detecting a speed of movement of the finger preceding the last location, and where recording the input to the touch-sensitive input area further comprises recording the speed of movement.

In some examples, the software may include software for automatically prompting, in response to the detecting of the termination of the input to the touch-sensitive input area, the user to provide additional input by touching the arc with the finger at one or more points along the length of the arc, thereby providing input to the touch-sensitive input area.

In some examples, the displaying of the arcuate input bar comprises displaying the arcuate input bar in a first color, and changing, in response to the detecting of the input to the touch-sensitive input area, the first color to a second color.

In some examples, the displaying of the arcuate input bar comprises changing, in response to the detecting of the termination of the input to the touch-sensitive input area, the second color to the first color.

In some examples, the displaying of the arcuate input bar comprises displaying the arcuate input bar in a first color, and where displaying the arcuate input bar further comprises changing, in response to the detecting of the termination of the input to the touch-sensitive input area, the first color to a second color.

A method for rapidly capturing user input is described. One or more embodiments of the method include displaying an arcuate input bar, the arcuate input bar being an arc with a radius originating from a segment of an edge defining at least a portion of a periphery of a surface of a housing, prompting a user to provide an input by touching the arc with a finger at one or more points along a length of the arc, thereby providing input to a touch-sensitive input area of a visual display screen, detecting the input to the touch-sensitive input area, including detecting a position along the arc of the input to the touch-sensitive input area, detecting a termination of the input to the touch-sensitive input area, and recording the input to the touch-sensitive input area as a last location of the input to the touch-sensitive input area preceding the detecting of the termination of the input to the touch-sensitive input area.

A system for rapidly capturing user input, the system comprising: a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and measuring a time between the prompting and the detecting of the termination, where recording the input to the touch-sensitive input area further comprises recording the time.

In some examples, the software may include software for displaying a cursor feature along the input bar at the position along the input bar of the input to the touch-sensitive input area.

In some examples, the software may include software for displaying at least one target along the input bar.

In some examples, the detecting of the input to the touch-sensitive input area further comprises detecting the position along the input bar of the input to the touch-sensitive input area when the position corresponds to at least one target along the input bar.

In some examples, the software may include software for displaying a response indicia separate from the input bar and varying the response indicia as a function of the position along the input bar of the input to the touch-sensitive input area.

In some examples, the software may include software for detecting the input to the touch-sensitive input area, including detecting a pattern of movements of the finger preceding the last location, where recording the input to the touch-sensitive input area further comprises recording the pattern of movements.

In some examples, the software may include software for detecting the input to the touch-sensitive input area, including detecting a speed of movement of the finger preceding the last location, where recording the input to the touch-sensitive input area further comprises recording the speed of movement.

In some examples, the software may include software for automatically prompting, in response to the detecting of the termination of the input to the touch-sensitive input area, the user to provide additional input by touching the input bar with the finger at one or more points along the length of the input bar, thereby providing input to the touch-sensitive input area.

In some examples, the displaying of the input bar comprises displaying the input bar in a first color and changing, in response to the detecting of the input to the touch-sensitive input area, the first color to a second color.

In some examples, the displaying of the input bar further comprises changing, in response to the detecting of the termination of the input to the touch-sensitive input area, the second color to the first color.

In some examples, the displaying of the input bar comprises displaying the input bar in a first color and changing, in response to the detecting of the termination of the input to the touch-sensitive input area, the first color to a second color.

In some examples, the software may include software for displaying a plurality of targets along the input bar.

In some examples, the detecting of the input to the touch-sensitive input area, where the detecting further comprises detecting the position along the input bar of the input to the touch-sensitive input area when the position corresponds to at least one target along the input bar.

In some examples, the software may include software for detecting the input to the touch-sensitive input area, including detecting a variation of speed of movement of the finger preceding the last location, and where recording the input to the touch-sensitive input area further comprises recording the variation of speed of movement.

A method for rapidly capturing user input is described. One or more embodiments of the method include displaying an input bar, prompting a user to provide an input by touching the input bar with a finger at one or more points along a length of the input bar, thereby providing input to a touch-sensitive input area of a visual display screen, detecting the input to the touch-sensitive input area, including detecting a position along the input bar of the input to the touch-sensitive input area, detecting a termination of the input to the touch-sensitive input area, recording the input to the touch-sensitive input area as a last location of the input to the touch-sensitive input area preceding the detecting of the termination of the input to the touch-sensitive input area, and measuring a time between the prompting and the detecting of the termination, wherein recording to the memory the input to the touch-sensitive input area further comprises recording the time.

A system for rapidly capturing user input, the system comprising: a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and detecting the input to the touch-sensitive input area, including detecting a degree of force applied for the input, wherein recording the input to the touch-sensitive input area further comprises recording the degree of force.

In some examples, the software may include software for displaying a cursor feature along the input bar at the position along the input bar of the input to the touch-sensitive input area.

In some examples, the software may include software for displaying at least one target along the input bar.

In some examples, the detecting of the input to the touch-sensitive input area further comprises detecting the position along the input bar of the input to the touch-sensitive input area when the position corresponds to at least one target along the input bar.

In some examples, the software may include software for displaying a response indicia separate from the input bar and varying the response indicia as a function of the position along the input bar of the input to the touch-sensitive input area.

In some examples, the software may include software for detecting the input to the touch-sensitive input area, including detecting a pattern of movements of the finger preceding the last location, where recording the input to the touch-sensitive input area further comprises recording the pattern of movements.

In some examples, the software may include software for detecting the input to the touch-sensitive input area, including detecting a speed of movement of the finger preceding the last location, where recording the input to the touch-sensitive input area further comprises recording the speed of movement.

In some examples, the software may include software for automatically prompting, in response to the detecting of the termination of the input to the touch-sensitive input area, the user to provide additional input by touching the input bar with the finger at one or more points along the length of the input bar, thereby providing input to the touch-sensitive input area.

In some examples, the displaying of the input bar comprises displaying the input bar in a first color and changing, in response to the detecting of the input to the touch-sensitive input area, the first color to a second color.

In some examples, the displaying of the input bar further comprises changing, in response to the detecting of the termination of the input to the touch-sensitive input area, the second color to the first color.

In some examples, the displaying of the input bar comprises displaying the input bar in a first color and changing, in response to the detecting of the termination of the input to the touch-sensitive input area, the first color to a second color.

In some examples, the software may include software for displaying a plurality of targets along the input bar.

In some examples, the detecting of the input to the touch-sensitive input area, where the detecting further comprises detecting the position along the input bar of the input to the touch-sensitive input area when the position corresponds to at least one target along the input bar.

In some examples, the software may include software for detecting the input to the touch-sensitive input area, including detecting a variation of speed of movement of the finger preceding the last location, and where recording the input to the touch-sensitive input area further comprises recording the variation of speed of movement.

A method for rapidly capturing user input is described. One or more embodiments of the method include displaying an input bar, prompting a user to provide an input by touching the input bar with a finger at one or more points along a length of the input bar, thereby providing input to a touch-sensitive input area of a visual display screen, detecting the input to the touch-sensitive input area, including detecting a position along the input bar of the input to the touch-sensitive input area, detecting a termination of the input to the touch-sensitive input area, recording, to memory, the input to the touch-sensitive input area as a last location of the input to the touch-sensitive input area preceding the detecting of the termination of the input to the touch-sensitive input area, and detecting the input to the touch-sensitive input area, including detecting a degree of force applied for the input, wherein recording the input to the touch-sensitive input area further comprises recording the degree of force.

A system for rapidly capturing user input, the system comprising: a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and detecting the input to the touch-sensitive input area, including detecting a pattern of movements of the finger preceding the last location, wherein recording the input to the touch-sensitive input area further comprises recording the pattern of movements.

In some examples, the software may include software for displaying a cursor feature along the input bar at the position along the input bar of the input to the touch-sensitive input area.

In some examples, the software may include software for displaying at least one target along the input bar.

In some examples, the detecting of the input to the touch-sensitive input area further comprises detecting the position along the input bar of the input to the touch-sensitive input area when the position corresponds to at least one target along the input bar.

In some examples, the software may include software for displaying a response indicia separate from the input bar and varying the response indicia as a function of the position along the input bar of the input to the touch-sensitive input area.

In some examples, the software may include software for detecting the input to the touch-sensitive input area, including detecting a pattern of movements of the finger preceding the last location, where recording the input to the touch-sensitive input area further comprises recording the pattern of movements.

In some examples, the software may include software for detecting the input to the touch-sensitive input area, including detecting a speed of movement of the finger preceding the last location, where recording the input to the touch-sensitive input area further comprises recording the speed of movement.

In some examples, the software may include software for automatically prompting, in response to the detecting of the termination of the input to the touch-sensitive input area, the user to provide additional input by touching the input bar with the finger at one or more points along the length of the input bar, thereby providing input to the touch-sensitive input area.

In some examples, the displaying of the input bar comprises displaying the input bar in a first color and changing, in response to the detecting of the input to the touch-sensitive input area, the first color to a second color.

In some examples, the displaying of the input bar further comprises changing, in response to the detecting of the termination of the input to the touch-sensitive input area, the second color to the first color.

In some examples, the displaying of the input bar comprises displaying the input bar in a first color and changing, in response to the detecting of the termination of the input to the touch-sensitive input area, the first color to a second color.

In some examples, the software may include software for displaying a plurality of targets along the input bar.

In some examples, the detecting of the input to the touch-sensitive input area, where the detecting further comprises detecting the position along the input bar of the input to the touch-sensitive input area when the position corresponds to at least one target along the input bar.

In some examples, the software may include software for detecting the input to the touch-sensitive input area, including detecting a variation of speed of movement of the finger preceding the last location, and where recording the input to the touch-sensitive input area further comprises recording the variation of speed of movement.

A method for rapidly capturing user input is described. One or more embodiments of the method include displaying an input bar, prompting a user to provide an input by touching the input bar with a finger at one or more points along a length of the input bar, thereby providing an input to a touch-sensitive input area of a visual display screen, detecting the input to the touch-sensitive input area, including detecting a position along the input bar of the input to the touch-sensitive input area, detecting a termination of the input to the touch-sensitive input area, recording to the memory the input to the touch-sensitive input area as a last location of the input to the touch-sensitive input area preceding the detecting of the termination of the input to the touch-sensitive input area, and detecting the input to the touch-sensitive input area, including detecting a pattern of movements of the finger preceding the last location, wherein recording the input to the touch-sensitive input area further comprises recording the pattern of movements.

A system for rapidly capturing user input, the system comprising: a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and detecting the input to the touch-sensitive input area, including detecting a speed of movement of the finger preceding the last location, wherein recording the input to the touch-sensitive input area further comprises recording the speed of movement of the finger preceding the last location.

In some examples, the software may include software for displaying a cursor feature along the input bar at the position along the input bar of the input to the touch-sensitive input area.

In some examples, the software may include software for displaying at least one target along the input bar.

In some examples, the detecting of the input to the touch-sensitive input area further comprises detecting the position along the input bar of the input to the touch-sensitive input area when the position corresponds to at least one target along the input bar.

In some examples, the software may include software for displaying a response indicia separate from the input bar and varying the response indicia as a function of the position along the input bar of the input to the touch-sensitive input area.

In some examples, the software may include software for detecting the input to the touch-sensitive input area, including detecting a pattern of movements of the finger preceding the last location, where recording the input to the touch-sensitive input area further comprises recording the pattern of movements.

In some examples, the software may include software for detecting the input to the touch-sensitive input area, including detecting a speed of movement of the finger preceding the last location, where recording the input to the touch-sensitive input area further comprises recording the speed of movement.

In some examples, the software may include software for automatically prompting, in response to the detecting of the termination of the input to the touch-sensitive input area, the user to provide additional input by touching the input bar with the finger at one or more points along the length of the input bar, thereby providing input to the touch-sensitive input area.

In some examples, the displaying of the input bar comprises displaying the input bar in a first color and changing, in response to the detecting of the input to the touch-sensitive input area, the first color to a second color.

In some examples, the displaying of the input bar further comprises changing, in response to the detecting of the termination of the input to the touch-sensitive input area, the second color to the first color.

In some examples, the displaying of the input bar comprises displaying the input bar in a first color and changing, in response to the detecting of the termination of the input to the touch-sensitive input area, the first color to a second color.

In some examples, the software may include software for displaying a plurality of targets along the input bar.

In some examples, the detecting of the input to the touch-sensitive input area, where the detecting further comprises detecting the position along the input bar of the input to the touch-sensitive input area when the position corresponds to at least one target along the input bar.

In some examples, the software may include software for detecting the input to the touch-sensitive input area, including detecting a variation of speed of movement of the finger preceding the last location, and where recording the input to the touch-sensitive input area further comprises recording the variation of speed of movement.

A method for rapidly capturing user input is described. One or more embodiments of the method include displaying an input bar, prompting a user to provide an input by touching the input bar with a finger at one or more points along a length of the input bar, thereby providing an input to a touch-sensitive input area of a visual display screen, detecting the input to the touch-sensitive input area, including detecting a position along the input bar of the input to the touch-sensitive input area, detecting a termination of the input to the touch-sensitive input area, recording the input to the touch-sensitive input area as a last location of the input to the touch-sensitive input area preceding the detecting of the termination of the input to the touch-sensitive input area, and detecting the input to the touch-sensitive input area, including detecting a speed of movement of the finger preceding the last location, wherein recording the input to the touch-sensitive input area further comprises recording the speed of movement of the finger preceding the last location.

A system for rapidly capturing user input, the system comprising: a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and detecting the input to the touch-sensitive input area, including detecting a speed of movement of the finger preceding the last location, wherein recording the input to the touch-sensitive input area further comprises recording the speed of movement of the finger preceding the last location.

In some examples, the software may include software for displaying a cursor feature along the input bar at the position along the input bar of the input to the touch-sensitive input area.

In some examples, the software may include software for displaying at least one target along the input bar.

In some examples, the detecting of the input to the touch-sensitive input area further comprises detecting the position along the input bar of the input to the touch-sensitive input area when the position corresponds to at least one target along the input bar.

In some examples, the software may include software for displaying a response indicia separate from the input bar and varying the response indicia as a function of the position along the input bar of the input to the touch-sensitive input area.

In some examples, the software may include software for detecting the input to the touch-sensitive input area, including detecting a pattern of movements of the finger preceding the last location, where recording the input to the touch-sensitive input area further comprises recording the pattern of movements.

In some examples, the software may include software for detecting the input to the touch-sensitive input area, including detecting a speed of movement of the finger preceding the last location, where recording the input to the touch-sensitive input area further comprises recording the speed of movement.

In some examples, the software may include software for automatically prompting, in response to the detecting of the termination of the input to the touch-sensitive input area, the user to provide additional input by touching the input bar with the finger at one or more points along the length of the input bar, thereby providing input to the touch-sensitive input area.

In some examples, the displaying of the input bar comprises displaying the input bar in a first color and changing, in response to the detecting of the input to the touch-sensitive input area, the first color to a second color.

In some examples, the displaying of the input bar further comprises changing, in response to the detecting of the termination of the input to the touch-sensitive input area, the second color to the first color.

In some examples, the displaying of the input bar comprises displaying the input bar in a first color and changing, in response to the detecting of the termination of the input to the touch-sensitive input area, the first color to a second color.

In some examples, the software may include software for displaying a plurality of targets along the input bar.

In some examples, the detecting of the input to the touch-sensitive input area, where the detecting further comprises detecting the position along the input bar of the input to the touch-sensitive input area when the position corresponds to at least one target along the input bar.

In some examples, the software may include software for detecting the input to the touch-sensitive input area, including detecting a variation of speed of movement of the finger preceding the last location, and where recording the input to the touch-sensitive input area further comprises recording the variation of speed of movement.

A method for rapidly capturing user input is described. One or more embodiments of the method include displaying an input bar, prompting a user to provide an input by touching the input bar with a finger at one or more points along a length of the input bar, thereby providing an input to a touch-sensitive input area of a visual display screen, detecting the input to the touch-sensitive input area, including detecting a position along the input bar of the input to the touch-sensitive input area, detecting a termination of the input to the touch-sensitive input area, recording the input to the touch-sensitive input area as a last location of the input to the touch-sensitive input area preceding the detecting of the termination of the input to the touch-sensitive input area, and detecting the input to the touch-sensitive input area, including detecting a speed of movement of the finger preceding the last location, wherein recording the input to the touch-sensitive input area further comprises recording the speed of movement of the finger preceding the last location.

A system for rapidly capturing user input, the system comprising: a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for performing the following steps: displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and measuring a time between initiation of the detecting of the input to the touch-sensitive input area and the detecting of the termination, wherein recording the input to the touch-sensitive input area further comprises recording the time.

In some examples, the software may include software for displaying a cursor feature along the input bar at the position along the input bar of the input to the touch-sensitive input area.

In some examples, the software may include software for displaying at least one target along the input bar.

In some examples, the detecting of the input to the touch-sensitive input area further comprises detecting the position along the input bar of the input to the touch-sensitive input area when the position corresponds to at least one target along the input bar.

In some examples, the software may include software for displaying a response indicia separate from the input bar and varying the response indicia as a function of the position along the input bar of the input to the touch-sensitive input area.

In some examples, the software may include software for detecting the input to the touch-sensitive input area, including detecting a pattern of movements of the finger preceding the last location, where recording the input to the touch-sensitive input area further comprises recording the pattern of movements.

In some examples, the software may include software for detecting the input to the touch-sensitive input area, including detecting a speed of movement of the finger preceding the last location, where recording the input to the touch-sensitive input area further comprises recording the speed of movement.

In some examples, the software may include software for automatically prompting, in response to the detecting of the termination of the input to the touch-sensitive input area, the user to provide additional input by touching the input bar with the finger at one or more points along the length of the input bar, thereby providing input to the touch-sensitive input area.

In some examples, the displaying of the input bar comprises displaying the input bar in a first color and changing, in response to the detecting of the input to the touch-sensitive input area, the first color to a second color.

In some examples, the displaying of the input bar further comprises changing, in response to the detecting of the termination of the input to the touch-sensitive input area, the second color to the first color.

In some examples, the displaying of the input bar comprises displaying the input bar in a first color and changing, in response to the detecting of the termination of the input to the touch-sensitive input area, the first color to a second color.

In some examples, the software may include software for displaying a plurality of targets along the input bar.

In some examples, the detecting of the input to the touch-sensitive input area, where the detecting further comprises detecting the position along the input bar of the input to the touch-sensitive input area when the position corresponds to at least one target along the input bar.

In some examples, the software may include software for detecting the input to the touch-sensitive input area, including detecting a variation of speed of movement of the finger preceding the last location, and where recording the input to the touch-sensitive input area further comprises recording the variation of speed of movement.

A method for rapidly capturing user input is described. One or more embodiments of the method include displaying an input bar, prompting a user to provide an input by touching the input bar with a finger at one or more points along a length of the input bar, thereby providing an input to a touch-sensitive input area of a visual display screen, detecting the input to the touch-sensitive input area, including detecting a position along the input bar of the input to the touch-sensitive input area, detecting a termination of the input to the touch-sensitive input area, recording the input to the touch-sensitive input area as a last location of the input to the touch-sensitive input area preceding the detecting of the termination of the input to the touch-sensitive input area, and measuring a time between initiation of the detecting of the input to the touch-sensitive input area and the detecting of the termination, wherein recording the input to the touch-sensitive input area further comprises recording the time.

A system for rapidly capturing user input, the system comprising: a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and detecting the input to the touch-sensitive input area, including detecting variations in speed of movements of the finger preceding the last location, wherein the recording the input to the touch-sensitive input area further comprises recording the variations in speed of movements.

In some examples, the software may include software for displaying a cursor feature along the input bar at the position along the input bar of the input to the touch-sensitive input area.

In some examples, the software may include software for displaying at least one target along the input bar.

In some examples, the detecting of the input to the touch-sensitive input area further comprises detecting the position along the input bar of the input to the touch-sensitive input area when the position corresponds to at least one target along the input bar.

In some examples, the software may include software for displaying a response indicia separate from the input bar and varying the response indicia as a function of the position along the input bar of the input to the touch-sensitive input area.

In some examples, the software may include software for detecting the input to the touch-sensitive input area, including detecting a pattern of movements of the finger preceding the last location, where recording the input to the touch-sensitive input area further comprises recording the pattern of movements.

In some examples, the software may include software for detecting the input to the touch-sensitive input area, including detecting a speed of movement of the finger preceding the last location, where recording the input to the touch-sensitive input area further comprises recording the speed of movement.

In some examples, the software may include software for automatically prompting, in response to the detecting of the termination of the input to the touch-sensitive input area, the user to provide additional input by touching the input bar with the finger at one or more points along the length of the input bar, thereby providing input to the touch-sensitive input area.

In some examples, the displaying of the input bar comprises displaying the input bar in a first color and changing, in response to the detecting of the input to the touch-sensitive input area, the first color to a second color.

In some examples, the displaying of the input bar further comprises changing, in response to the detecting of the termination of the input to the touch-sensitive input area, the second color to the first color.

In some examples, the displaying of the input bar comprises displaying the input bar in a first color and changing, in response to the detecting of the termination of the input to the touch-sensitive input area, the first color to a second color.

In some examples, the software may include software for displaying a plurality of targets along the input bar.

In some examples, the detecting of the input to the touch-sensitive input area, where the detecting further comprises detecting the position along the input bar of the input to the touch-sensitive input area when the position corresponds to at least one target along the input bar.

In some examples, the software may include software for detecting the input to the touch-sensitive input area, including detecting a variation of speed of movement of the finger preceding the last location, and where recording the input to the touch-sensitive input area further comprises recording the variation of speed of movement.

A method for rapidly capturing user input is described. One or more embodiments of the method include displaying an input bar, prompting a user to provide an input by touching the input bar with a finger at one or more points along a length of the input bar, thereby providing an input to a touch-sensitive input area of a visual display screen, detecting the input to the touch-sensitive input area, including detecting a position along the input bar of the input to the touch-sensitive input area, detecting a termination of the input to the touch-sensitive input area, recording the input to the touch-sensitive input area as a last location of the input to the touch-sensitive input area preceding the detecting of the termination of the input to the touch-sensitive input area, and detecting the input to the touch-sensitive input area, including detecting variations in speed of movements of the finger preceding the last location, wherein the recording the input to the touch-sensitive input area further comprises recording the variations in speed of movements.

A system for rapidly capturing user input, the system comprising: a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and detecting the input to the touch-sensitive input area, including detecting a pattern of movements of the finger preceding the last location, wherein recording the input to the touch-sensitive input area further comprises recording the pattern of movements.

In some examples, the software may include software for displaying a cursor feature along the input bar at the position along the input bar of the input to the touch-sensitive input area.

In some examples, the software may include software for displaying at least one target along the input bar.

In some examples, the detecting of the input to the touch-sensitive input area further comprises detecting the position along the input bar of the input to the touch-sensitive input area when the position corresponds to at least one target along the input bar.

In some examples, the software may include software for displaying a response indicia separate from the input bar and varying the response indicia as a function of the position along the input bar of the input to the touch-sensitive input area.

In some examples, the software may include software for detecting the input to the touch-sensitive input area, including detecting a pattern of movements of the finger preceding the last location, where recording the input to the touch-sensitive input area further comprises recording the pattern of movements.

In some examples, the software may include software for detecting the input to the touch-sensitive input area, including detecting a speed of movement of the finger preceding the last location, where recording the input to the touch-sensitive input area further comprises recording the speed of movement.

In some examples, the software may include software for automatically prompting, in response to the detecting of the termination of the input to the touch-sensitive input area, the user to provide additional input by touching the input bar with the finger at one or more points along the length of the input bar, thereby providing input to the touch-sensitive input area.

In some examples, the displaying of the input bar comprises displaying the input bar in a first color and changing, in response to the detecting of the input to the touch-sensitive input area, the first color to a second color.

In some examples, the displaying of the input bar further comprises changing, in response to the detecting of the termination of the input to the touch-sensitive input area, the second color to the first color.

In some examples, the displaying of the input bar comprises displaying the input bar in a first color and changing, in response to the detecting of the termination of the input to the touch-sensitive input area, the first color to a second color.

In some examples, the software may include software for displaying a plurality of targets along the input bar.

In some examples, the detecting of the input to the touch-sensitive input area, where the detecting further comprises detecting the position along the input bar of the input to the touch-sensitive input area when the position corresponds to at least one target along the input bar.

In some examples, the software may include software for detecting the input to the touch-sensitive input area, including detecting a variation of speed of movement of the finger preceding the last location, and where recording the input to the touch-sensitive input area further comprises recording the variation of speed of movement.

A method for rapidly capturing user input is described. One or more embodiments of the method include displaying an input bar, prompting a user to provide an input by touching the input bar with a finger at one or more points along a length of the input bar, thereby providing an input to a touch-sensitive input area of a visual display screen, detecting the input to the touch-sensitive input area, including detecting a position along the input bar of the input to the touch-sensitive input area, detecting a termination of the input to the touch-sensitive input area, recording to the memory the input to the touch-sensitive input area as a last location of the input to the touch-sensitive input area preceding the detecting of the termination of the input to the touch-sensitive input area, and detecting the input to the touch-sensitive input area, including detecting a pattern of movements of the finger preceding the last location, wherein recording the input to the touch-sensitive input area further comprises recording the pattern of movements.

A method for rapidly capturing user input is described. One or more embodiments of the method include displaying an input bar, prompting a user to provide an input by touching the input bar with a finger at one or more points along a length of the input bar, thereby providing an input to a touch-sensitive input area of a visual display screen, detecting the input to the touch-sensitive input area, including detecting a position along the input bar of the input to the touch-sensitive input area, detecting a termination of the input to the touch-sensitive input area, recording to the memory the input to the touch-sensitive input area as a last location of the input to the touch-sensitive input area preceding the detecting of the termination of the input to the touch-sensitive input area, and detecting the input to the touch-sensitive input area, including detecting a pause in movement of the finger preceding the last location, wherein recording the input to the touch-sensitive input area further comprises recording the pause in movement.

A system for rapidly capturing user input, the system comprising: a visual display screen having a surface area, a touch-sensitive input area, the touch-sensitive input area being across at least a portion of the surface area, a memory, and a processor operatively coupled to the visual display screen, the memory and the touch-sensitive input area, wherein the processor comprises software for displaying an input bar; prompting a user to provide an input by touching the input bar with a finger at one or more points along a length of the input bar, thereby providing input to the touch-sensitive input area; detecting the input to the touch-sensitive input area, including detecting a position along the input bar of the input to the touch-sensitive input area; detecting a termination of the input to the touch-sensitive input area; recording to the memory the input to the touch-sensitive input area as a last location of the input to the touch-sensitive input area preceding the detecting of the termination of the input to the touch-sensitive input area; and detecting the input to the touch-sensitive input area, including detecting a pause in movement of the finger preceding the last location, wherein recording the input to the touch-sensitive input area further comprises recording the pause in movement.

In some examples, the software may include software for displaying a cursor feature along the input bar at the position along the input bar of the input to the touch-sensitive input area.

In some examples, the software may include software for displaying at least one target along the input bar.

In some examples, the detecting of the input to the touch-sensitive input area further comprises detecting the position along the input bar of the input to the touch-sensitive input area when the position corresponds to at least one target along the input bar.

In some examples, the software may include software for displaying a response indicia separate from the input bar and varying the response indicia as a function of the position along the input bar of the input to the touch-sensitive input area.

In some examples, the software may include software for detecting the input to the touch-sensitive input area, including detecting a pattern of movements of the finger preceding the last location, where recording the input to the touch-sensitive input area further comprises recording the pattern of movements.

In some examples, the software may include software for detecting the input to the touch-sensitive input area, including detecting a speed of movement of the finger preceding the last location, where recording the input to the touch-sensitive input area further comprises recording the speed of movement.

In some examples, the software may include software for automatically prompting, in response to the detecting of the termination of the input to the touch-sensitive input area, the user to provide additional input by touching the input bar with the finger at one or more points along the length of the input bar, thereby providing input to the touch-sensitive input area.

In some examples, the displaying of the input bar comprises displaying the input bar in a first color and changing, in response to the detecting of the input to the touch-sensitive input area, the first color to a second color.

In some examples, the displaying of the input bar further comprises changing, in response to the detecting of the termination of the input to the touch-sensitive input area, the second color to the first color.

In some examples, the displaying of the input bar comprises displaying the input bar in a first color and changing, in response to the detecting of the termination of the input to the touch-sensitive input area, the first color to a second color.

In some examples, the software may include software for displaying a plurality of targets along the input bar.

In some examples, the detecting of the input to the touch-sensitive input area, where the detecting further comprises detecting the position along the input bar of the input to the touch-sensitive input area when the position corresponds to at least one target along the input bar.

In some examples, the software may include software for detecting the input to the touch-sensitive input area, including detecting a variation of speed of movement of the finger preceding the last location, and where recording the input to the touch-sensitive input area further comprises recording the variation of speed of movement.

Some of the functional units described in this specification have been labeled as modules, or components, to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

While the invention herein disclosed has been described by means of specific embodiments, examples and applications thereof, numerous modifications and variations could be made thereto by those skilled in the art without departing from the scope of the invention set forth in the claims.

What is claimed is:

1. A system for rapidly capturing user input comprising:
   a visual display screen having a surface area;
   a touch-sensitive input area, the touch-sensitive input area being across at least a portion of the surface area;
   a memory;
   a processor operatively coupled to the visual display screen, the memory and the touch-sensitive input area, wherein the processor comprises software for performing the following steps:
   displaying an input bar;
   prompting a user to provide an input, wherein the input is provided by the user touching the input bar with a finger at one or more points along a length of the input bar, thereby providing input to the touch-sensitive input area;
   detecting the input to the touch-sensitive input area, including detecting a position along the input bar of the input to the touch-sensitive input area;
   detecting a termination of the input to the touch-sensitive input area;
   recording to the memory the input to the touch-sensitive input area as a last location of the input to the touch-sensitive input area preceding the detecting of the termination of the input to the touch-sensitive input area;
   detecting said input to the touch-sensitive input area, including detecting a pattern of movements of said finger preceding said last location;
   said recording to said memory said input to the touch-sensitive input area, wherein said recording further comprises recording the pattern of movements, wherein the pattern of movements indicates a degree of the user's response to the prompting.

2. The system for rapidly capturing user input of claim 1, comprising:
   said processor, wherein said processor comprises said software for performing the following additional step:
   displaying a cursor feature along the input bar at said position along said input bar of said input to said touch-sensitive input area.

3. The system for rapidly capturing user input of claim 1, comprising:
   said processor, wherein said processor comprises said software for performing the following additional step:
   displaying at least one target along said input bar.

4. The system for rapidly capturing user input of claim 3, comprising:
   said processor, wherein said processor comprises said software for performing the following additional step:
   said detecting the input to the touch-sensitive input area, wherein said detecting further comprises detecting said position along the input bar of the input to the touch-sensitive input area when said position corresponds to at least one target along said input bar.

5. The system for rapidly capturing user input of claim 1, comprising:
   said processor, wherein said processor comprises said software for performing the following additional step:
   displaying a response indicia separate from the input bar and varying the response indicia as a function of said position along the input bar of the input to the touch-sensitive input area.

6. The system for rapidly capturing user input of claim 1, comprising:
   said processor, wherein said processor comprises said software for performing the following additional step:
   displaying a plurality of targets along said input bar.

7. The system for rapidly capturing user input of claim 1, comprising:
   said processor, wherein said processor comprises said software for performing the following additional steps:
   measuring a time between initiation of the detecting of the input to the touch-sensitive input area and said detecting said termination; and
   said recording to said memory said input to the touch-sensitive input area, wherein said recording further comprises recording the time between initiation of the detecting of the input to the touch-sensitive input area and the detecting of the termination.

8. The system for rapidly capturing user input of claim 1, further comprising:
   said processor, wherein said processor comprises said software for performing the following additional steps:
   detecting said input to the touch-sensitive input area, including detecting a degree of force applied for said input; and
   said recording to said memory said input to the touch-sensitive input area, wherein said recording further comprises recording the degree of force.

9. The system for rapidly capturing user input of claim 1, further comprising:
   said processor, wherein said processor comprises said software for performing the following additional steps:
   detecting said input to the touch-sensitive input area, including detecting a variation of speed of movement of said finger preceding said last location;
   said recording to said memory said input to the touch-sensitive input area, wherein said recording further comprises recording the variation of speed of movement.

10. The system for rapidly capturing user input of claim 1, further comprising:
   said processor, wherein said processor comprises said software of performing the following additional step:
   automatically prompting, in response to said detecting said termination of said input to said touch-sensitive input area, said user to provide additional input by touching said input bar with said finger at one or more points along said length of the input bar, thereby providing input to said touch-sensitive input area.

11. The system for rapidly capturing user input further of claim 1, comprising:
said processor, wherein said processor comprises said software for performing the following additional steps:
said displaying said input bar, said displaying said input bar comprises displaying said input bar in a first color; and
said displaying said input bar, said displaying said input bar further comprising changing, in response to said detecting said input to the touch-sensitive input area, the first color to a second color.

12. The system for rapidly capturing user input of claim 11, further comprising:
said processor, wherein said processor comprises said software for performing the following further step:
said displaying said input bar, said displaying said input bar further comprising changing, in response to said detecting said termination of said input to the touch-sensitive input area.

13. The system for rapidly capturing user input of claim 1, further comprising:
said processor, wherein said processor comprises said software for performing the following additional steps:
said displaying said input bar, said displaying said input bar comprises displaying said input bar in a first color; and
said displaying said input bar, said displaying said input bar further comprising changing, in response to said detecting said termination of said input to the touch-sensitive input area, the first color to a second color.

14. The system for rapidly capturing user input of claim 1, wherein said input bar includes an arc.

15. The system for rapidly capturing user input of claim 1, further comprising:
said processor, wherein said processor comprises said software for performing the following additional steps:
in response to said detecting said termination of said input to said touch-sensitive input area, displaying a new user input prompt on the display screen.

16. The system for rapidly capturing user input of claim 1, further comprising:
said prompting the user to provide the input by touching the input bar with the finger at one or more points along the length of the input bar, wherein the prompting comprises displaying a Likert item on the display screen.

17. The system for rapidly capturing user input of claim 1, further comprising:
said detecting the input to the touch-sensitive input area, including detecting the position along the input bar of the input to the touch-sensitive input area, wherein the position along the input bar corresponds to a level of the user's agreement or disagreement on a symmetric agree-disagree scale.

18. The system for rapidly capturing user input of claim 1, further comprising:
said recording to said memory said input to the touch-sensitive input area, wherein said recording further comprises recording the pattern of movements, wherein the pattern of movements indicates a degree of the user's conviction.

19. The system for rapidly capturing user input of claim 1, further comprising:
measuring a time between said prompting and said detecting said termination; and
said recording to said memory said input to the touch-sensitive input area, wherein said recording further comprises recording the time between said prompting and said detecting said termination.

20. The system for rapidly capturing user input of claim 5, further comprising:
said displaying the response indicia separate from the input bar, wherein the response indicia consists of Likert scale responses.

21. The system for rapidly capturing user input of claim 9, further comprising:
said recording to said memory said input to the touch-sensitive input area, wherein said recording further comprises recording a pause in movement.

* * * * *